(12) United States Patent
Boehringer et al.

(10) Patent No.: US 7,718,666 B2
(45) Date of Patent: May 18, 2010

(54) PYRIDO [2,1-A] ISOQUINOLINE DERIVATIVES

(75) Inventors: Markus Boehringer, Moehlin (CH); Bernd Kuhn, Riehen (CH); Thomas Luebbers, Loerrach (DE); Patrizio Mattei, Riehen (CH); Robert Narquizian, St. Louis (FR); Hans Peter Wessel, Schliengen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/870,268

(22) Filed: Jun. 17, 2004

(65) Prior Publication Data
US 2004/0259902 A1   Dec. 23, 2004

(30) Foreign Application Priority Data
Jun. 20, 2003   (EP) ............................... 03013405

(51) Int. Cl.
C07D 487/02 (2006.01)
A61K 31/4745 (2006.01)
(52) U.S. Cl. ........................................ 514/290; 546/79
(58) Field of Classification Search ................... 546/95, 546/79; 514/294, 290
See application file for complete search history.

(56) References Cited

U.S. PATENT DOCUMENTS

| | | | |
|---|---|---|---|
| 4,550,114 A | 10/1985 | White | |
| 5,455,351 A | 10/1995 | Kempf et al. | |
| 6,011,155 A | 1/2000 | Villhauer et al. | |
| 6,110,949 A | 8/2000 | Villhauer | |
| 6,124,305 A | 9/2000 | Villhauer | |
| 6,172,081 B1 | 1/2001 | Damon | |
| 6,303,661 B1 | 10/2001 | Demuth et al. | |
| 6,319,893 B1 | 11/2001 | Demuth et al. | |
| 6,727,261 B2 * | 4/2004 | Gobbi et al. ................. | 514/294 |
| 2002/0071838 A1 | 6/2002 | Demuth et al. | |
| 2004/0259903 A1 | 12/2004 | Boehringer et al. | |

FOREIGN PATENT DOCUMENTS

| | | |
|---|---|---|
| DE | 19616486 A1 | 10/1997 |
| DE | 19616486 C2 | 10/1997 |
| DE | 19834591 | 2/2000 |
| EP | 524004 A1 | 1/1993 |
| WO | WO 95/01976 | 1/1995 |
| WO | WO 96/10018 | 4/1996 |
| WO | WO 98/19998 | 5/1998 |
| WO | WO 99/38501 A2 | 8/1999 |
| WO | WO 99/38501 A3 | 8/1999 |
| WO | WO 00/08002 | 2/2000 |
| WO | WO 0034241 | 6/2000 |
| WO | WO 01/19805 | 3/2001 |
| WO | WO 0134594 | 5/2001 |
| WO | WO 01/40180 | 6/2001 |
| WO | WO 01/55105 | 8/2001 |
| WO | WO 0162266 | 8/2001 |
| WO | WO 0230890 | 4/2002 |
| WO | WO 03/055881 | 7/2003 |

OTHER PUBLICATIONS

Sudre et al., Dabetes, "Chronic inhibition of circulating dipeptidyl peptidase IV by FE 999011 delays the occurrence of diabetes in male Zucker diabetic fatty rats", May 2002, vol. 51, pp. 1461-1469.*
Agarwal, A., et. al., Synth. Commun. (1993) 23, 1101-1110.
Ali, et. al., Pak. J. Sci. Ind. Res., 36, pp. 502-510 (1993).
Carrera, G.M., et. al., Synlett (1994) 1, 93-94.
Collins, J.L., et. al. J. Med Chem. (1998) 41, 5037-5054.
Freedman, J., et. al., J. Heterocycl. Chem. (1990) 27, 343-346.
Francis, et. al., Tetrahedron Ltrs., 28, pp. 5133-5136 (1987).
Golfier, et. al., J. Heterocycl. Chem., 10, pp. 989-991 (1973).
Goto, et. al., Chem. Pharm. Bull, 19, pp. 2050-2057 (1971).
Helv. Chim. Acta (1958) 41, 119.
Horne, et. al., Heterocycles, 39, pp. 139-153 (1994).
Lipp, et. al., Eur. J. Med. Chem., 30 pp. 219-225 (1995).
Novartis AG, Expert Opinion on Therapeutic Patents, Ashley Publications, GB, vol. 10, No. 12, pp. 1937-1942 (2000).
Qizhuang, Y., et.al., J. Med. Chem. (1989) 32; 478-486.
P. Kocienski, Protecting Groups, Thieme Verlag Stuttgart, NY (1994) pp. 192-201.
Schunack, et. al., Z. Naturforschung; 42b, pp. 238-242 (1987).
Singh, et. al., Ind. J. Chem., 22B, pp. 1177-1178 (1983).
Tetrahedron (1974), 30, 2157.
Tetrahedron Lett. (1984) 25, 3515.
Weintraub, P. M., J. Med. Chem, 15, pp. 419-420 (1972).
Chem. Ber 95, 2132 (1962).
J. Org. Chem (1998) 63, 6715.

* cited by examiner

Primary Examiner—D. Margaret Seaman
Assistant Examiner—Niloofar Rahmani
(74) Attorney, Agent, or Firm—George W. Johnston; Dennis P. Tramaloni; Samuel H. Megerditchain

(57) ABSTRACT

The present invention relates to compounds of formula (I)

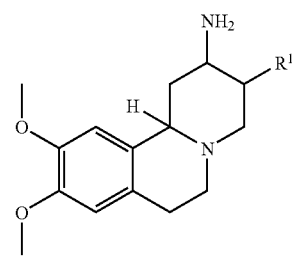

wherein $R^1$ is as defined in the description, and pharmaceutically acceptable salts thereof. The compounds are useful for the treatment and/or prophylaxis of diseases which are associated with DPP-IV, such as diabetes, particularly non-insulin dependent diabetes mellitus, and impaired glucose tolerance.

13 Claims, No Drawings

PYRIDO [2,1-A] ISOQUINOLINE DERIVATIVES

BACKGROUND OF THE INVENTION

The enzyme dipeptidyl peptidase IV (EC.3.4.14.5, abbreviated in the following as DPP-IV) is involved in the regulation of the activities of several hormones. In particular DPP-IV is degrading efficiently and rapidly glucagon like peptide 1 (GLP-1), which is one of the most potent stimulator of insulin production and secretion. Inhibiting DPP-IV would potentiate the effect of endogenous GLP-1, and lead to higher plasma insulin concentrations. In patients suffering from impaired glucose tolerance and type 2 diabetes mellitus, higher plasma insulin concentration would moderate the dangerous hyperglycaemia and accordingly reduce the risk of tissue damage. Consequently, DPP-IV inhibitors have been suggested as drug candidates for the treatment of impaired glucose tolerance and type 2 diabetes mellitus (e.g. Villhauer, WO98/19998). Other related state of the art can be found in WO 99/38501, DE 19616486, DE 19834591, WO 01/40180, WO 01/55105, U.S. Pat. No. 6,110,949, WO 00/34241 and U.S. Pat. No. 6,011,155.

SUMMARY OF THE INVENTION

The present invention provides compounds of the formula (I)

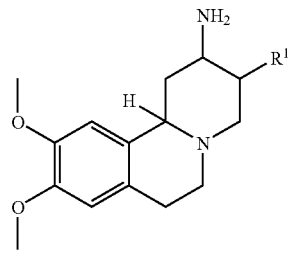

wherein
$R^1$ is selected from

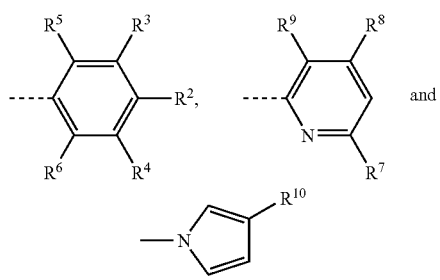

$R^2$ is hydrogen or lower alkoxy;
$R^3$, $R^4$, $R^5$ and $R^6$ are each independently selected from hydrogen, lower alkyl, halogenated lower alkyl, halogen or cycloalkyl; provided that $R^2$, $R^3$, $R^4$, $R^5$ and $R^6$ are not all hydrogen;
$R^7$, $R^8$ and $R^9$ are each independently hydrogen, lower alkyl, lower alkoxy, lower hydroxyalkyl or halogenated lower alkyl; provided that $R^7$, $R^8$ and $R^9$ are not all hydrogen;
$R^{10}$ is lower alkyl or halogenated lower alkyl;

and pharmaceutically acceptable salts thereof.

The compounds of the present invention are useful in the treatment of type II diabetes mellitus.

DETAILED DESCRIPTION OF THE INVENTION

The present invention provides a compound of formula (I)

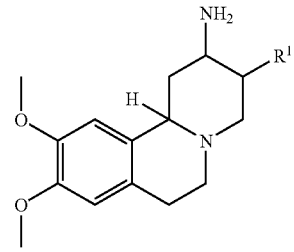

wherein
$R^1$ is selected from the group consisting of

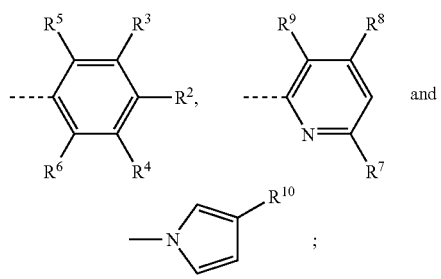

$R^2$ is hydrogen or lower alkoxy;
$R^3$, $R^4$, $R^5$ and $R^6$ are each independently selected from the group consisting of hydrogen, lower alkyl, halogenated lower alkyl, halogen and cycloalkyl; provided that $R^2$, $R^3$, $R^4$, $R^5$ and $R^6$ are not all hydrogen;
$R^7$, $R^8$ and $R^9$ are each independently selected from the group consisting of hydrogen, lower alkyl, lower alkoxy, lower hydroxyalkyl and halogenated lower alkyl; provided that $R^7$, $R^8$ and $R^9$ are not all hydrogen;
$R^{10}$ is lower alkyl or halogenated lower alkyl;

or a pharmaceutically acceptable salt thereof.

We have found novel DPP-IV inhibitors that very efficiently lower plasma glucose levels. Consequently, the compounds of the present invention are useful for the treatment and/or prophylaxis of diabetes, particularly non-insulin dependent diabetes mellitus, and/or impaired glucose tolerance, as well as other conditions wherein the amplification of action of a peptide normally inactivated by DPP-IV gives a therapeutic benefit. Surprisingly, the compounds of the present invention can also be used in the treatment and/or prophylaxis of obesity, inflammatory bowel disease, Colitis Ulcerosa, Morbus Crohn, and/or metabolic syndrome or β-cell protection. Furthermore, the compounds of the present invention can be used as diuretic agents and for the treatment and/or prophylaxis of hypertension.

Unexpectedly, the compounds of the present invention exhibit improved therapeutic and pharmacological properties compared to other DPP-IV inhibitors known in the art, such as e.g. in context with pharmacokinetics and bioavailability.

Unless otherwise indicated, the following definitions are set forth to illustrate and define the meaning and scope of the various terms used to describe the invention herein.

In this specification the term "lower" is used to mean a group consisting of one to six, preferably of one to four carbon atom(s).

The term "halogen" refers to fluorine, chlorine, bromine and iodine, with fluorine and chlorine being preferred. Most preferred halogen is chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to six carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl and ethyl, with methyl being especially preferred.

The term "halogenated lower alkyl" refers to a lower alkyl group wherein at least one of the hydrogens of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with fluoromethyl being especially preferred.

The term "alkoxy" refers to the group R'—O—, wherein R' is alkyl. The term "lower-alkoxy" refers to the group R'—O—, wherein R' is lower alkyl. Examples of lower alkoxy groups are e.g. methoxy, ethoxy, propoxy, isopropoxy, butoxy, isobutoxy and hexyloxy, with methoxy being especially preferred.

The term "cycloalkyl" refers to a monovalent carbocyclic radical of three to six, preferably three to five carbon atoms. This term is further exemplified by radicals such as cyclopropyl, cyclobutyl, cyclopentyl and cyclohexyl, with cyclopropyl being preferred.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment, the present invention relates to compounds having the formula (I)

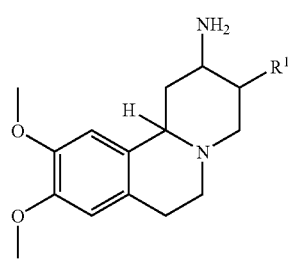

(I)

wherein
$R^1$ is selected from

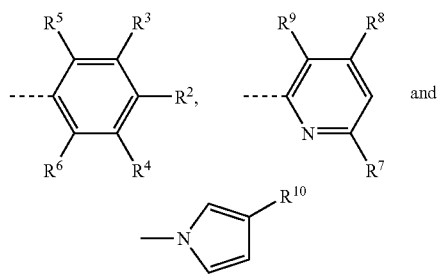

and $R^2$ is hydrogen or lower alkoxy;

$R^3$, $R^4$, $R^5$ and $R^6$ are each independently selected from hydrogen, lower alkyl, halogenated lower alkyl, halogen or cycloalkyl; provided that $R^2$, $R^3$, $R^4$, $R^5$ and $R^6$ are not all hydrogen;

$R^7$, $R^8$ and $R^9$ are each independently hydrogen, lower alkyl or lower alkoxy; provided that $R^7$, $R^8$ and $R^9$ are not all hydrogen;

$R^{10}$ is lower alkyl or halogenated lower alkyl;

and pharmaceutically acceptable salts thereof.

In one embodiment, $R^1$ is

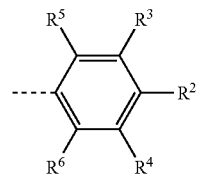

wherein $R^2$ is hydrogen or lower alkoxy and $R^3$, $R^4$, $R^5$ and $R^6$ are each independently selected from hydrogen, lower alkyl, halogenated lower alkyl, halogen or cycloalkyl; provided that $R^2$, $R^3$, $R^4$, $R^5$ and $R^6$ are not all hydrogen.

Preferable lower alkoxy residue $R^2$ is methoxy.

Preferable lower alkyl residues in $R^3$, $R^4$, $R^5$ and $R^6$ are methyl, ethyl, and isopropyl, with methyl being especially preferred. Preferable halogenated lower alkyl residue in $R^3$, $R^4$, $R^5$ and $R^6$ is fluoromethyl. Preferable halogen residue in $R^3$, $R^4$, $R^5$ and $R^6$ is chloro. Preferable cycloalkyl residue in $R^3$, $R^4$, $R^5$ and $R^6$ is cyclopropyl.

In one preferable embodiment, $R^2$, $R^4$, $R^5$ and $R^6$ are hydrogen and $R^3$ is lower alkyl, halogenated lower alkyl, halogen or cycloalkyl, with lower alkyl such as methyl or ethyl, halogenated lower alkyl such as fluoromethyl or halogen such as chloro being especially preferred.

In another preferable embodiment, $R^2$, $R^4$ and $R^5$ are hydrogen and $R^3$ and $R^6$ are each independently lower alkyl, halogenated lower alkyl, halogen or cycloalkyl, with lower alkyl such as methyl or halogen such as chloro being especially preferred.

In another embodiment of the present invention, $R^1$ is

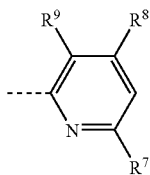

wherein $R^7$, $R^8$ and $R^9$ are each independently hydrogen, lower alkyl, lower alkoxy, lower hydroxyalkyl or halogenated lower alkyl; provided that $R^7$, $R^8$ and $R^9$ are not all hydrogen.

Preferable lower alkyl residues in $R^7$, $R^8$ and $R^9$ are methyl and ethyl, with methyl being especially preferred. Preferable lower alkoxy residue in $R^7$, $R^8$ and $R^9$ is methoxy.

In a preferable embodiment, $R^7$ and $R^9$ are hydrogen and $R^8$ is lower alkyl such as methyl or ethyl, or lower alkoxy such as methoxy.

In a further preferable embodiment, $R^7$ and $R^9$ are hydrogen and $R^8$ is lower hydroxyalkyl such as hydroxymethyl, or halogenated lower alkyl such as fluoromethyl.

In still another embodiment of the present invention, $R^1$ is

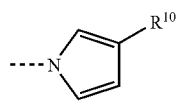

wherein $R^{10}$ is lower alkyl or halogenated lower alkyl.

Preferable lower alkyl residues $R^{10}$ are methyl and ethyl, with methyl being especially preferred. Preferable halogenated lower alkyl residue $R^{10}$ is fluoromethyl.

Preferred compounds of general formula (I) are those selected from the group consisting of:

rac-9,10-dimethoxy-3β-m-tolyl-1,3,4,6,7,11bβ-hexahydro-2H-pyrido[2,1-a]isoquinolin-2-ylamine hydrochloride,
rac-9,10-dimethoxy-3β-m-tolyl-1,3,4,6,7,11bβ-hexahydro-2H-pyrido[2,1-a]isoquinolin-2β-ylamine,
9,10-dimethoxy-3(R)-m-tolyl-1,3,4,6,7,11b(R)-hexahydro-2H-pyrido[2,1-a]isoquinolin-2(S)-ylamine,
9,10-dimethoxy-3(S)-m-tolyl-1,3,4,6,7,11b(S)-hexahydro-2H-pyrido[2,1-a]isoquinolin-2(R)-ylamine,
rac-9,10-dimethoxy-3β-m-tolyl-1,3,4,6,7,11bβ-hexahydro-2H-pyrido[2,1-a]isoquinolin-2α-ylamine,
9,10-dimethoxy-3(S)-m-tolyl-1,3,4,6,7,11b(S)-hexahydro-2H-pyrido[2,1-a]isoquinolin-2(S)-ylamine,
9,10-dimethoxy-3(R)-m-tolyl-1,3,4,6,7,11bβ(R)-hexahydro-2H-pyrido[2,1-a]isoquinolin-2(R)-ylamine,
rac-9,10-dimethoxy-3β-(4-methyl-pyridin-2-yl)-1,3,4,6,7,11bβ-hexahydro-2H-pyrido[2,1-a]isoquinolin-2α-ylamine,
9,10-dimethoxy-3(S)-(4-methyl-pyridin-2-yl)-1,3,4,6,7,11b(S)-hexahydro-2H-pyrido[2,1-a]isoquinolin-2(S)-ylamine,
9,10-dimethoxy-3(R)-(4-methyl-pyridin-2-yl)-1,3,4,6,7,11b(R)-hexahydro-2H-pyrido[2,1-a]isoquinolin-2(R)-ylamine,
rac-9,10-dimethoxy-3β-(6-methyl-pyridin-2-yl)-1,3,4,6,7,11bβ-hexahydro-2H-pyrido[2,1-a]isoquinolin-2α-ylamine,
rac-9,10-dimethoxy-3β-(6-methyl-pyridin-2-yl)-1,3,4,6,7,11bβ-hexahydro-2H-pyrido[2,1-a]isoquinolin-2β-ylamine,
rac-9,10-dimethoxy-3β-(5-methyl-pyridin-2-yl)-1,3,4,6,7,11bβ-hexahydro-2H-pyrido[2,1-a]isoquinolin-2α-ylamine,
rac-9,10-dimethoxy-3 β-(5-methyl-pyridin-2-yl)-1,3,4,6,7,11bβ-hexahydro-2H-pyrido[2,1-a]isoquinolin-2β-ylamine,
rac-9,10-dimethoxy-3β-(4-methyl-pyridin-2-yl)-1,3,4,6,7,11bβ-hexahydro-2H-pyrido[2,1-a]isoquinolin-2β-ylamine,
9,10-dimethoxy-3(R)-(4-methyl-pyridin-2-yl)-1,3,4,6,7,11b(R)-hexahydro-2H-pyrido[2,1-a]isoquinolin-2(S)-ylamine,
9,10-dimethoxy-3 (S)-(4-methyl-pyridin-2-yl)-1,3,4,6,7,11b(S)-hexahydro-2H-pyrido[2,1-a]isoquinolin-2(R)-ylamine,
rac-9,10-dimethoxy-3β-(3-methyl-pyridin-2-yl)-1,3,4,6,7,11bβ-hexahydro-2H-pyrido[2,1-a]isoquinolin-2α-ylamine,
rac-9,10-dimethoxy-3β-(3-methyl-pyridin-2-yl)-1,3,4,6,7,11bβ-hexahydro-2H-pyrido[2,1-a]isoquinolin-2β-ylamine,
rac-3β-(4-ethyl-pyridin-2-yl)-9,10-dimethoxy-1,3,4,6,7,11bβ-hexahydro-2H-pyrido[2,1-a]isoquinolin-2α-ylamine,
rac-3β-(4-ethyl-pyridin-2-yl)-9,10-dimethoxy-1,3,4,6,7,11bβ-hexahydro-2H-pyrido[2,1-a]isoquinolin-2β-ylamine,
rac-3β-(4-ethyl-phenyl)-9,10-dimethoxy-1,3,4,6,7,11bβ-hexahydro-2H-pyrido[2,1-a]isoquinolin-2α-ylamine,
rac-3β-(4-ethyl-phenyl)-9,10-dimethoxy-1,3,4,6,7,11bβ-hexahydro-2H-pyrido[2,1-a]isoquinolin-2β-ylamine,
rac-3β-(2,5-dimethyl-phenyl)-9,10-dimethoxy-1,3,4,6,7,11bβ-hexahydro-2H-pyrido[2,1-a]isoquinolin-2α-ylamine,
rac-3β-(3-cyclopropyl-phenyl)-9,10-dimethoxy-1,3,4,6,7,11bβ-hexahydro-2H-pyrido[2,1-a]isoquinolin-2α-ylamine,
rac-3β-(6-methoxy-pyridin-2-yl)-9,10-dimethoxy-1,3,4,6,7,11bβ-hexahydro-2H-pyrido[2,1-a]isoquinolin-2α-ylamine,
rac-3β-(2,5-dimethyl-phenyl)-9,10-dimethoxy-1,3,4,6,7,11bβ-hexahydro-2H-pyrido[2,1-a]isoquinolin-2β-ylamine,
rac-3β-(3-isopropyl-phenyl)-9,10-dimethoxy-1,3,4,6,7,11bβ-hexahydro-2H-pyrido[2,1-a]isoquinolin-2α-ylamine,
rac-3β-(3-cyclopropyl-phenyl)-9,10-dimethoxy-1,3,4,6,7,11bβ-hexahydro-2H-pyrido[2,1-a]isoquinolin-2β-ylamine,
rac-3β-(3-fluormethyl-phenyl)-9,10-dimethoxy-1,3,4,6,7,11bβ-hexahydro-2H-pyrido[2,1-a]isoquinolin-2β-ylamine,
rac-3β-(3-fluormethyl-phenyl)-9,10-dimethoxy-1,3,4,6,7,11bβ-hexahydro-2H-pyrido[2,1-a]isoquinolin-2α-ylamine,
rac-3β-(4-methoxy-2-methyl-phenyl)-9,10-dimethoxy-1,3,4,6,7,11bβ-hexahydro-2H-pyrido[2,1-a]isoquinolin-2α-ylamine,
rac-9,10-dimethoxy-3β-(3-methyl-pyrrol-1-yl)-1,3,4,6,7,11bβ-hexahydro-2H-pyrido[2,1-a]isoquinolin-2α-ylamine,
rac-3β-(3-chloro-phenyl)-9,10-dimethoxy-1,3,4,6,7,11bβ-hexahydro-2H-pyrido[2,1-a]isoquinolin-2β-ylamine hydrochloride,
rac-3β-(3-chloro-phenyl)-9,10-dimethoxy-1,3,4,6,7,11bβ-hexahydro-2H-pyrido[2,1-a]isoquinolin-2α-ylamine hydrochloride, rac-[2-(2α-amino-9,10-dimethoxy-1,3,4,6,7,11bβ-hexahydro-2H-pyrido[2,1-a]isoquinolin-3β-yl)-pyridin-4-yl]-methanol, rac-3β-(4-fluoromethyl-pyridin-2-yl)-9,10-dimethoxy-1,3,4,6,7,11bβ-hexahydro-2H-pyrido[2,1-a]isoquinolin-2α-ylamine hydrochloride, rac-3β-(4-fluoromethyl-pyridin-2-yl)-9,10-dimethoxy-1,3,4,6,7,11bβ-hexahydro-2H-pyrido[2,1-a]isoquinolin-2α-ylamine, and pharmaceutically acceptable salts thereof.

Especially preferred compounds of general formula (I) are those selected from the group consisting of:

9,10-dimethoxy-3(R)-m-tolyl-1,3,4,6,7,11b(R)-hexahydro-2H-pyrido[2,1-a]isoquinolin-2(S)-ylamine, 9,10-dimethoxy-3(S)-m-tolyl-1,3,4,6,7,11b(S)-hexahydro-2H-pyrido[2,1-a]isoquinolin-2(S)-ylamine, 9,10-dimethoxy-3(S)-(4-methyl-pyridin-2-yl)-1,3,4,6,7,11b(S)-hexahydro-2H-pyrido[2,1-a]isoquinolin-2(S)-ylamine, 9,10-dimethoxy-3(R)-(4-methyl-pyridin-2-yl)-1,3,4,6,7,11b(R)-hexahydro-2H-pyrido[2,1-a]isoquinolin-2(S)-ylamine, rac-3β-(4-ethyl-pyridin-2-yl)-9,10-dimethoxy-1,3,4,6,7,11bβ-hexahydro-2H-pyrido[2,1-a]isoquinolin-2α-ylamine, rac-3β-(4-ethyl-pyridin-2-yl)-9,10-dimethoxy-1,3,4,6,7,11bβ-hexahydro-2H-pyrido[2,1-a]isoquinolin-2β-ylamine, rac-3β-(2,5-dimethyl-phenyl)-9,10-dimethoxy-1,3,4,6,7,11bβ-hexahydro-2H-pyrido[2,1-a]isoquinolin-2α-ylamine, rac-3β-(2,5-dimethyl-phenyl)-9,10-dimethoxy-1,3,4,6,7,11bβ-hexahydro-2H-pyrido[2,1-a]isoquinolin-2β-ylamine, rac-3β-(3-chloro-phenyl)-9,10-dimethoxy-1,3,4,6,7,11bβ-hexahydro-2H-pyrido[2,1-a]isoquinolin-2β-ylamine hydrochloride, rac-3β-(3-chloro-phenyl)-9,10-dimethoxy-1,3,4,6,7,11bβ-hexahydro-2H-pyrido[2,1-a]isoquinolin-2α-ylamine hydrochloride, rac-3β-(3-fluormethyl-phenyl)-9,10-dimethoxy-1,3,4,6,7,11bβ-hexahydro-2H-pyrido[2,1-a]isoquinolin-2β-ylamine, rac-3β-(3-fluormethyl-phenyl)-9,10-dimethoxy-1,3,4,6,7,11bβ-hexahydro-2H-pyrido[2,1-a]isoquinolin-2α-ylamine, rac-9,10-dimethoxy-3β-(3-methyl-pyrrol-1-yl)-1,3,4,6,7,11bβ-hexahydro-2H-pyrido[2,1-a]isoquinolin-2α-ylamine, and pharmaceutically acceptable salts thereof.

The compounds of formula I have three or more asymmetric carbon atoms and can exist in the form of optically pure enantiomers, mixtures of diastereomers, racemates, or mixtures of diastereoisomeric racemates. The invention embraces all of these forms.

In a preferable embodiment, $R^1$ and the hydrogen in position 11b of the pyrido[2,1a]isoquinoline backbone are in cis-configuration, whereas the amino group in position 2 of the pyrido[2,1a]isoquinoline backbone is in trans-configuration, i.e.

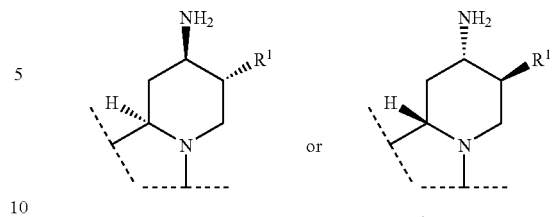

In another preferable embodiment, $R^1$, the amino group in position 2 and the hydrogen in position 11b of the pyrido[2,1a]isoquinoline backbone are all in cis-configuration, i.e.

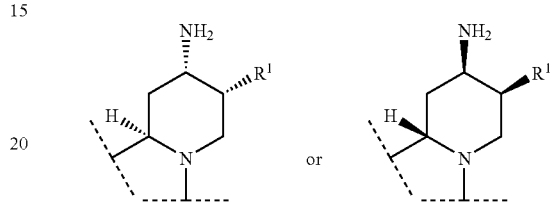

It will be appreciated, that the compounds of general formula (I) in this invention may be derivatised at functional groups to provide derivatives which are capable of conversion back to the parent compound in vivo.

The present invention also relates to a process for the manufacture of compounds of formula I. The compounds of the present invention can be prepared as indicated in Schemes 1 and 2 below:

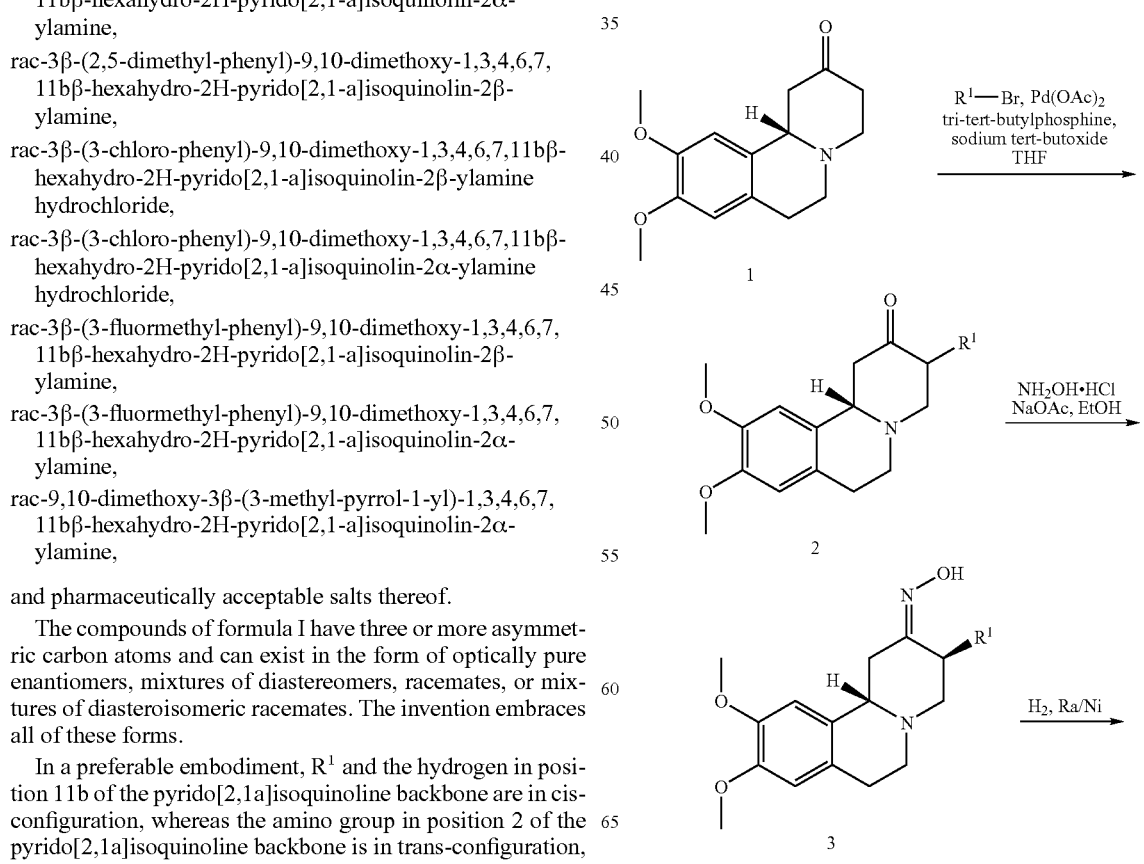

Scheme 1

-continued

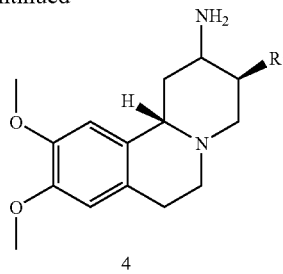

4

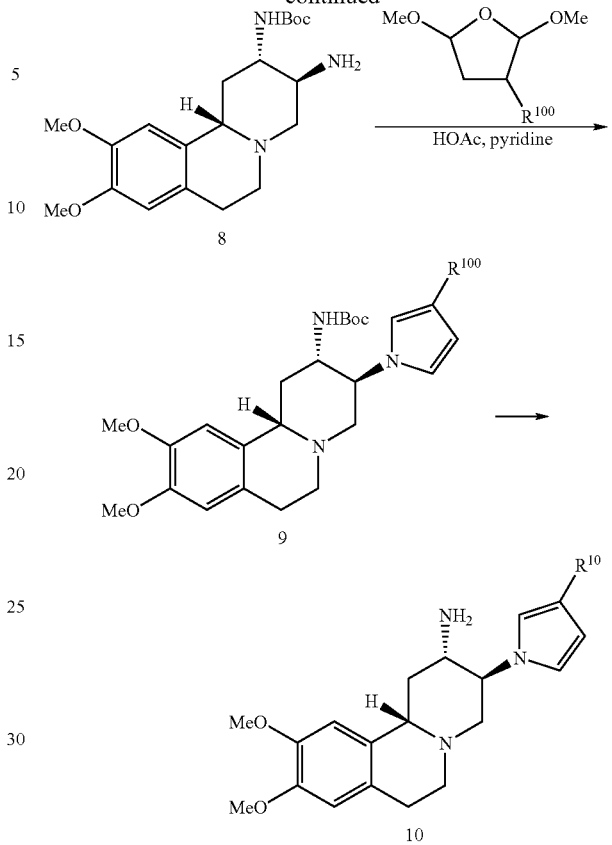

The synthesis of 3-phenyl and 3-pyridyl derivatives 4 is outlined in Scheme 1 and can be achieved using the ketone 1 as starting material, a compound well known in the art [Chem. Ber. 95, 2132 (1962)]. Reaction of 1 with an aryl halide leads in a metal-mediated reaction and under suitable conditions (base, exclusion of oxygen) to the aryl- and heteroaryl ketones 3. Preferred metal reagents are palladium catalysts.

The ketones are then converted to amino functions by known methods. One possibility is the conversion of the keto group to an oxime of formula 3 using hydroxylamine hydrochloride and sodium acetate in a solvent such as ethanol. Oximes can be reduced by e.g. catalytic hydrogenation to the final compounds 4.

The 2α, 3β, 11bβ isomer is usually the predominant product which is easily separated from the other stereoisomer by chromatography.

The separation of the enantiomeric mixture in its chiral components can be achieved by chromatography on a chiral phase.

Scheme 2

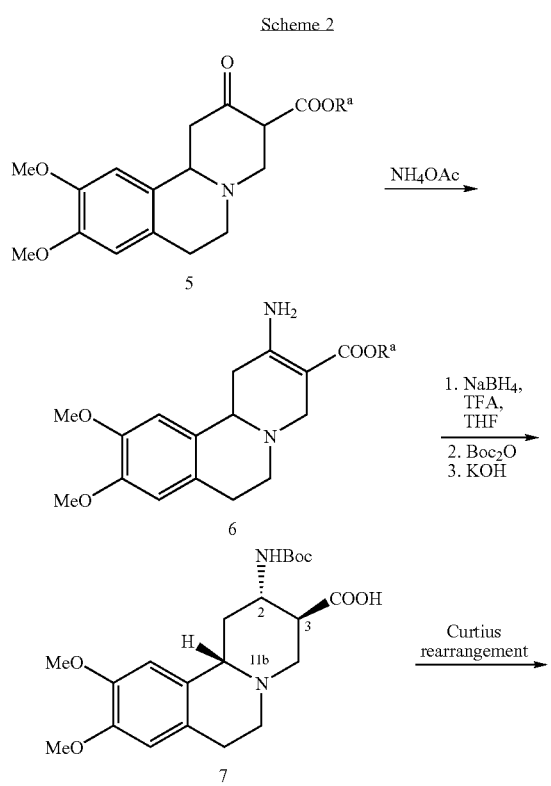

$R^a$=methyl or ethyl; $R^{100}$=$R^{10}$ or C(O)—$R^{101}$, with $R^{101}$=H, lower alkyl, or halogenated lower alkyl.

The synthesis of pyrrol-1-yl derivatives 10 is outlined in Scheme 2 and starts with the β-ketoester 5 ($R^a$=methyl or ethyl), a compound well known in the art (Helv. Chim. Acta 1958, 41, 119). Reaction of 5 with ammonium acetate in a solvent such as methanol produces the β-enamino-ester 6, which is reduced, preferably with sodium borohydride/trifluoroacetic acid, to the corresponding the β-amino-ester. The amino group is then converted to the tert-butyl carbamate and the ester group hydrolyzed using a base, preferably potassium or sodium hydroxide in a water/tetrahydrofuran mixture, to yield the acid 7. The 2α,3β,11bβ isomer of 7 is the predominant product and is easily separated from the other possible diastereomers, e.g., by crystallization.

Acid 7 is elaborated into amine 8 via a Curtius rearrangement. A preferred protocol for this conversion is a two-step sequence, where the acid is first heated with a mixture of diphenylphosphoryl azide, a base (e.g., triethylamine), and 2-(trimethylsilyl)-ethanol, in a solvent such as toluene, at about 70-110° C. The 2-(trimethylsilyl)-ethyl carbamate intermediate is then deprotected with a fluoride, e.g., tetrabutylammonium fluoride in THF, at about 50° C. (Tetrahedron Lett. 1984, 25, 3515).

Reaction of amine 8 with an appropriately substituted 2,5-dimethoxytetra-hydrofuran in acetic acid/pyridine (J. Org. Chem. 1998, 63, 6715) at about 100° C. produces 9, which is converted to the final compound of formula 10, using methods known in the art.

The invention further relates to compounds of formula (I) as defined above, when manufactured according to a process as defined above.

As described above, the compounds of formula (I) of the present invention can be used as medicaments for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably non-insulin dependent diabetes mellitus and/or impaired glucose tolerance. Furthermore, the compounds of the present invention can be used as diuretic agents or for the treatment and/or prophylaxis of hypertension.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for use as therapeutic active substances for the treatment and/or prophylaxis of non-insulin dependent diabetes mellitus and/or impaired glucose tolerance.

Furthermore, the invention relates to compounds as defined above for use as diuretic agents or for use as therapeutic active substances for the treatment and/or prophylaxis of hypertension.

In another embodiment, the invention relates to a method for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for the treatment and/or prophylaxis of non-insulin dependent diabetes mellitus and/or impaired glucose tolerance, which method comprises administering a compound as defined above to a human being or animal. Furthermore, the invention relates to a method for the treatment and/or prophylaxis as defined above, wherein the disease is hypertension or wherein a diuretic agent has a beneficial effect.

The invention further relates to the use of compounds as defined above for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for the treatment and/or prophylaxis of non-insulin dependent diabetes mellitus and/or impaired glucose tolerance. Furthermore, the invention relates to the use as defined above, wherein the disease is hypertension or to the use as diuretic agent.

In addition, the invention relates to the use of compounds as defined above for the preparation of medicaments for the treatment and/or prophylaxis of diseases which are associated with DPP-IV such as diabetes, particularly non-insulin dependent diabetes mellitus, impaired glucose tolerance, inflammatory bowel disease, Colitis Ulcerosa, Morbus Crohn, obesity, and/or metabolic syndrome or β-cell protection, preferably for the treatment and/or prophylaxis of non-insulin dependent diabetes mellitus and/or impaired glucose tolerance. Such medicaments comprise a compound as defined above. Furthermore, the invention relates to the use as defined above, wherein the disease is hypertension or the use for the preparation of diuretic agents.

In context with the methods and uses defined above, the following diseases relate to a preferred embodiment: diabetes, particularly non-insulin dependent diabetes mellitus, impaired glucose tolerance, obesity, and/or metabolic syndrome or β-cell protection, preferably non-insulin dependent diabetes mellitus and/or impaired glucose tolerance.

The compounds of formula (I) can be manufactured by the methods given below, by the methods given in the Examples or by analogous methods. Appropriate reaction conditions for the individual reaction steps are known to the person skilled in the art. Starting materials are either commercially available or can be prepared by methods analogous to the methods given below or in the Examples or by methods known in the art.

The following tests were carried out in order to determine the activity of the compounds of formula I.

Activity of DPP-IV inhibitors are tested with natural human DPP-IV derived from a human plasma pool or with recombinant human DPP-IV. Human citrate plasma from different donors is pooled, filtered through a 0.2 micron membrane under sterile conditions and aliquots of 1 ml are shock frozen and stored at −120° C. until used. In the colorimetric DPP-IV assay 5 to 10 µl human plasma and in the fluorometric assay 1.0 µl of human plasma in a total assay volume of 100 µl is used as an enzyme source. The cDNA of the human DPP-IV sequence of amino acid 31- to 766, restricted for the N-terminus and the transmembrane domain, is cloned into *Pichia pastoris*. Human DPP-IV is expressed and purified from the culture medium using conventional column chromatography including size exclusion and anion and cation chromatography. The purity of the final enzyme preparation of Coomassie blue SDS-PAGE is >95%. In the calorimetric DPP-IV assay 20 ng rec.-h DPP-IV and in the fluorometric assay 2 ng rec-h DPP-IV in a total assay volume of 100 µl is used as an enzyme source.

In the fluorogenic assay Ala-Pro-7-amido-4-trifluoromethylcoumarin (Calbiochem No 125510) is used as a substrate. A 20 mM stock solution in 10% DMF/H$_2$O is stored at −20° C. until use. In IC$_{50}$ determinations a final substrate concentration of 50 µM is used. In assays to determine kinetic parameters as $K_m$, $V_{max}$, $K_i$, the substrate concentration is varied between 10 µM and 500 µM.

In the calorimetric assay H-Ala-Pro-pNA.HCl (Bachem L-1115) is used as a substrate. A 10 mM stock solution in 10% MeOH/H2O is stored at −20° C. until use. In IC$_{50}$ determinations a final substrate concentration of 200 µM is used. In assays to determine kinetic parameters as $K_m$, $V_{max}$, $K_i$, the substrate concentration is varied between 100 µM and 2000 µM.

Fluorescence is detected in a Perkin Elmer Luminescence Spectrometer LS 50B at an excitation wavelength of 400 nm and an emission wavelength of 505 nm continuously every 15 seconds for 10 to 30 minutes. Initial rate constants are calculated by best fit linear regression.

The absorption of pNA liberated from the calorimetric substrate is detected in a Packard SpectraCount at 405 nm continuosly every 2 minutes for 30 to 120 minutes. Initial rate constants are calculated by best fit linear regression.

DPP-IV activity assays are performed in 96 well plates at 37° C. in a total assay volume of 100 µl. The assay buffer consists of 50 mM Tris/HCl pH 7.8 containing 0.1 mg/ml BSA and 100 mM NaCl. Test compounds are solved in 100% DMSO, diluted to the desired concentration in 10% DMSO/H$_2$O. The final DMSO concentration in the assay is 1% (v/v). At this concentration enzyme inactivation by DMSO is <5%.

Compounds are with (10 minutes at 37° C.) and without preincubation with the enzyme. Enzyme reactions are started with substrate application followed by immediate mixing.

$IC_{50}$ determinations of test compounds are calculated by non-linear best fit regression of the DPP-IV inhibition of at least 5 different compound concentrations. Kinetic parameters of the enzyme reaction are calculated at least 5 different substrate concentrations and at least 5 different test compound concentrations.

The compounds of the present invention exhibit $IC_{50}$ values of 0.1 nM to 10 μM, more preferably of 0.1-100 nM, as shown in the following table:

| Example | $IC_{50}$ [μM] |
|---|---|
| 2 | 0.029 |
| 9 | 0.0115 |
| 30 | 0.005 |
| 33 | 0.0054 |
| 35 | 0.0042 |

The compounds of formula I and/or their pharmaceutically acceptable salts can be used as medicaments, e.g. in the form of pharmaceutical preparations for enteral, parenteral or tropical administration. They can be administered, for example, perorally, e.g. in the form of tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

The following Examples serve to illustrate the present invention in more detail. They are, however, not intended to limit its scope in any manner.

EXAMPLES

Example 1 rac-9,10-Dimethoxy-3β-m-tolyl-1,3,4,6,7,11bβ-hexahydro-2H-pyrido[2,1-a]isoquinolin-2-ylamine hydrochloride

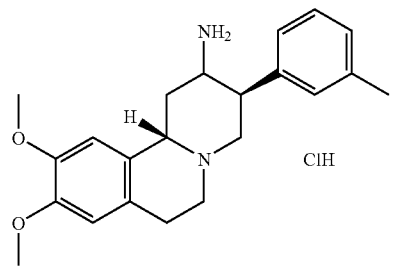

a) rac-9,10-dimethoxy-3β-m-tolyl-1,3,4,6,7,11bβ-hexahydro-2H-pyrido[2,1-a]-isoquinolin-2-one Palladium acetate (21 mg, 0.01 mmol), sodium tert-butoxide (276 mg, 2.87 mmol), and tri-tert-butylphosphine (23 mg, 0.115 mmol) were dissolved under argon in tetrahydrofuran (2 mL). 3-Bromotoluene (164 mg, 0.957 mmol) and rac-9,10-dimethoxy-1,3,4,6,7,11bβ-hexahydro-2H-benzo[a]quinolizin-2-one (250 mg, 0.957 mmol) were sequentially added under flow of argon and stirred at room temperature for 12 hours. The reaction mixture was diluted with water and extracted 3 times with ether. The combined organic layers were washed with water, brine, and dried over sodium sulfate, filtered and concentrated in vacuo to give the crude product. The crude product was chromatographed on silica gel (ether) to afford 139 mg (0.39 mmol, 41%) of rac-9,10-dimethoxy-3β-m-tolyl-1,3,4,6,7,11bβ-hexahydro-2H-pyrido[2,1-a]isoquinolin-2-one as a light yellow solid.

MS (ISP): 343.3 (M+H)$^+$.

$^1$H NMR (CDCl$_3$): δ=7.29-7.24 (m, 1H), 6.99-6.73 (m, 2H), 6.62 (s, 1H), 6.59 (s, 1H), 3.96-3.92 (m, 1H), 3.89-3.80 (m, 6H, 2 methoxy groups), 3.76-3.72 (m, 1H), 3.43-3.38 (m, 1H), 3.19-3.93 (m, 5H), 2.79-2.64 (m, 3H), 2.32 (s, 3H, Ar—CH$_3$).

b) rac-9,10-Dimethoxy-3β-m-tolyl-1,3,4,6,7,11bβ-hexahydro-2H-pyrido[2,1-a]-isoquinolin-2-ylamine hydrochloride rac-9,10-Dimethoxy-3β-m-tolyl-1,3,4,6,7,11bβ-hexahydro-2H-pyrido[2,1-a]isoquinolin-2-one (62 mg), NaOAc (16 mg) and hydroxylamine hydrochloride (14 mg) were dissolved in ethanol (2 ml) and stirred at room temperature for 3 hours. Water (2 ml) and Ni—Al alloy (100 mg) were added. NaOH as a 32% aqueous solution (0.35 ml) was added dropwise to this suspension. Hydrogen evolved and the reaction mixture turned warm. The reaction mixture was stirred at room temperature over night. The same amount of base and Ni—Al alloy was added and the reaction was stirred at room temperature for further 3 hours. The reaction mixture was filtered and the solution extracted 3 times with methylene chloride. The combined organic layers were washed with brine, dried over sodium sulfate, filtered and concentrated in vacuo. Chromatography on silica gel (CH$_2$Cl$_2$/MeOH/NH$_4$OH aq 25% 100/5/1) afforded the product as a mixture of the cis- and the trans-diastereoisomers. The amines were dissolved in methylene chloride and HCl in ether was added. The solvent was evaporated to leave the product (46 mg, 67%) as an orange solid.
MS (ISP): 353.3 (M+H)$^+$.

Example 2 rac-9,10-Dimethoxy-3β-m-tolyl-1,3,4,6,7,11bβ-hexahydro-2H-pyrido[2,1-a]isoquinolin-2β-ylamine

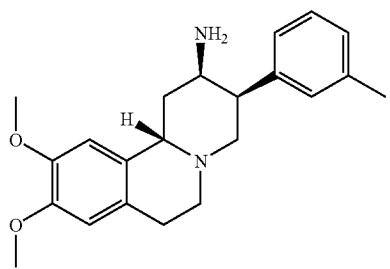

a) rac-9,10-Dimethoxy-3β-m-tolyl-1,3,4,6,7,11bβ-hexahydro-2H-pyrido[2,1-a]isoquinolin-2-one A mixture of palladium acetate (1.72 g), sodium tert-butoxide (22.01 g) and rac-9,10-dimethoxy-1,3,4,6,7,11bβ-hexahydro-2H-benzo[a]quinolizin-2-one (20.0 g) [D. Beke, C. Szantay, Chem. Ber. 95, 2132 (1962)] were evaporated under high vacuum at 80° C. and charged with argon three to five times. Degassed tetrahydrofuran (220 mL) was added at room temperature under argon. The reaction mixture was stirred for 15 minutes at room temperature, and tri-tert-butylphosphine (1.86 g) and 3-bromotoluene (13.75 g) were added simultaneously with a syringe. The reaction mixture was stirred at 20-25° C. under argon for 4 hours. The crude reaction mixture was poured on ice/water (1 L), and the precipitate was filtered off. The filtrate was extracted twice with tert-butylmethyl ether. The organic phase was concentrated, the residue was combined with the precipitate obtained above and dissolved in methylene chloride, washed with water and brine. The organic layer was dried over magnesium sulfate and filtered. The solvent was evaporated. The residue was purified by column chromatography (silica gel, 325 g) using methylene chloride/ethyl acetate 1:1 as eluent to yield rac-9,10-dimethoxy-3β-m-tolyl-1,3,4,6,7,11bβ-hexahydro-2H-pyrido[2,1-a]isoquinolin-2-one (11.9 g) as a light yellow solid.
MS (ISP): 352.4 (M+H)$^+$.

b) rac-9,10-Dimethoxy-3β-m-tolyl-1,3,4,6,7,11bβ-hexahydro-2H-pyrido[2,1-a]isoquinolin-2-one oxime To a suspension of rac-9,10-dimethoxy-3β-m-tolyl-1,3,4,6,7,11bβ-hexahydro-2H-pyrido[2,1-a]isoquinolin-2-one (26.95 g) in ethanol (500 mL) were added hydroxylamine hydrochloride (5.82 g) and sodium acetate (6.92 g). The reaction mixture was stirred at room temperature for 4.5 hours, cold water (1.5 L) was added. The precipitate was filtered off, and the cake was washed with cold water and dried over P$_2$O$_5$ under high vacuum over night to obtain rac-9,10-dimethoxy-3β-m-tolyl-1,3,4,6,7,11bβ-hexahydro-2H-pyrido[2,1-a]isoquinolin-2-one oxime (26.48 g) as a colourless solid.
MS (ISP): 367.4 (M+H)$^+$.

c) rac-9,10-Dimethoxy-3β-m-tolyl-1,3,4,6,7,11bβ-hexahydro-2H-pyrido[2,1-a]isoquinolin-2β-ylamine To a solution of rac-9,10-dimethoxy-3β-m-tolyl-1,3,4,6,7,11bβ-hexahydro-2H-pyrido[2,1-a]isoquinolin-2-one oxime (30.2 g) in ethanol/dioxane 1:1 (2400 mL) was added the wet Ra/Ni (150 g). The reaction mixture was evaporated and charged with hydrogen, conc. NH$_4$OH (45 mL) was added with the help of a syringe, and the hydrogenation was started. After 4.5 hours at 1.1 bar and room temperature, the reaction mixture was filtered over a fine filter (caution!), the catalyst was washed with ethanol, the filtrate concentrated. The residue was chromatographed over silica gel using methylene chloride/methanol/conc. ammonia 95:5:0.5 and 90:10:0.9 as eluent to obtain the title compound (3.0 g) as a yellow powder. This product was eluted first during chromatography.
MS (ISP): 353.4 (M+H)$^+$.

Example 3

9,10-Dimethoxy-3(R)-m-tolyl-1,3,4,6,7,11bβ(R)-hexahydro-2H-pyrido[2,1-a]-isoquinolin-2(S)-ylamine

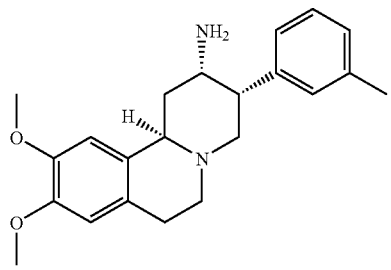

The title compound was obtained after separation of rac-9,10-dimethoxy-3β-m-tolyl-1,3,4,6,7,11bβ-hexahydro-2H-pyrido[2,1-a]isoquinolin-2β-ylamine (Example 2) through a Chiralpak AD column with 15% ethanol/heptane as eluent. The retention time was 115 minutes.
MS (ISP): 353.3 (M+H)$^+$, [α]$_D$+156° (c 0.558, chloroform).

Example 4

9,10-Dimethoxy-3(S)-m-tolyl-1,3,4,6,7,11b(S)-hexahydro-2H-pyrido[2,1-a]isoquinolin-2(R)-ylamine

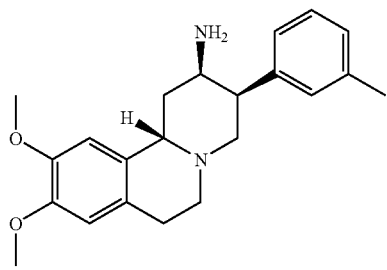

The title compound was obtained after separation of rac-9,10-dimethoxy-3β-m-tolyl-1,3,4,6,7,11bβ-hexahydro-2H-pyrido[2,1-a]isoquinolin-2β-ylamine (Example 2) through a Chiralpak AD column with 15% ethanol/heptane as eluent. The retention time was 159 minutes.

MS (ISP): 353.3 (M+H)$^+$, [α]$_D$ −154° (c 0.523, chloroform).

Example 5 rac-9,10-Dimethoxy-3β-m-tolyl-1,3,4,6,7,11bβ-hexahydro-2H-pyrido[2,1-a]isoquinolin-2α-ylamine

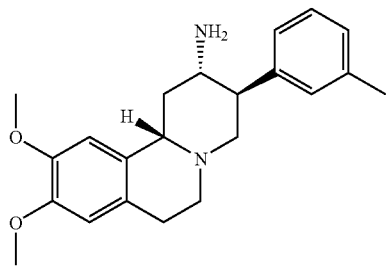

The product was obtained in the final chromatography described in Example 2 eluting as second compound (20.2 g) as light yellow crystals.

MS (ISP): 353.4 (M+H)$^+$.

Example 6

9,10-Dimethoxy-3(S)-m-tolyl-1,3,4,6,7,11b(S)-hexahydro-2H-pyrido[2,1-a]isoquinolin-2(S)-ylamine

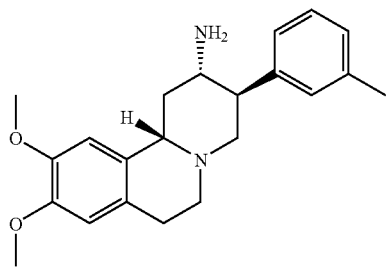

The title compound was obtained after separation of rac-9,10-dimethoxy-3β-m-tolyl-1,3,4,6,7,11bβ-hexahydro-2H-pyrido[2,1-a]isoquinolin-2α-ylamine (Example 5) through a Chiralpak AD column with 20% isopropanol/heptane as eluent. The retention time was 270 minutes.

MS (ISP): 353.4 (M+H)$^+$, [α]$_D$ −57° (c 0.345, chloroform).

Example 7

9,10-Dimethoxy-3(R)-m-tolyl-1,3,4,6,7,11bβ(R)-hexahydro-2H-pyrido[2,1-a]isoquinolin-2(R)-ylamine

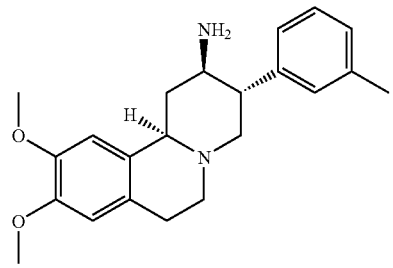

The title compound was obtained after separation of rac-9,10-dimethoxy-3β-m-tolyl-1,3,4,6,7,11bβ-hexahydro-2H-pyrido[2,1-a]isoquinolin-2α-ylamine (Example 5) through a Chiralpak AD column with 20% isopropanol/heptane as eluent. The retention time was 158 minutes.

MS (ISP): 353.4 (M+H)$^+$, [α]$_D$ +57° (c 0.545, chloroform).

Example 8 rac-9,10-Dimethoxy-3β-(4-methyl-pyridin-2-yl)-1,3,4,6,7,11bβ-hexahydro-2H-pyrido[2,1-a]isoquinolin-2α-ylamine

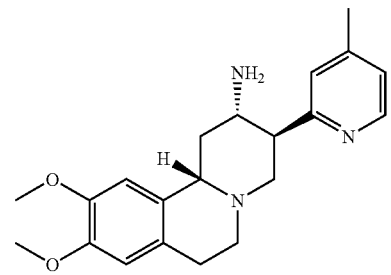

The title compound was prepared in analogy to Example 2. It was obtained as an orange-red powder. This product was eluted second during chromatography (cf. Example 15).

MS (ISP): 354.3 (M+H)$^+$.

Example 9

9,10-Dimethoxy-3(S)-(4-methyl-pyridin-2-yl)-1,3,4,6,7,11b(S)-hexahydro-2H-pyrido[2,1a]isoquinolin-2(S)-ylamine

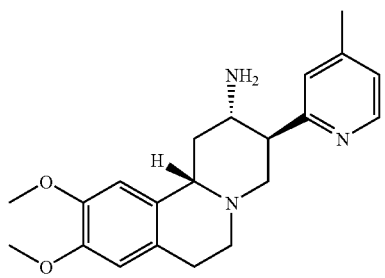

The title compound was obtained after separation of rac-9,10-Dimethoxy-3β-(4-methyl-pyridin-2-yl)-1,3,4,6,7,11bβ-hexahydro-2H-pyrido[2,1-a]isoquinolin-2α-ylamine (Example 8) through a Chiralpak AD column with 20% isopropanol/heptane as eluent. The retention time was 350 minutes.

MS (ISP): 354.3 (M+H)$^+$, [α]$_D$ −67.5° (c 0.527, chloroform).

Example 10

9,10-Dimethoxy-3(R)-(4-methyl-pyridin-2-yl)-1,3,4,6,7,11b(R)-hexahydro-2H-pyrido[2,1-a]isoquinolin-2(R)-ylamine

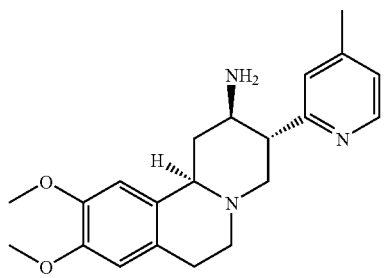

The title compound was obtained after separation of rac-9,10-Dimethoxy-3β-(4-methyl-pyridin-2-yl)-1,3,4,6,7,11bβ-hexahydro-2H-pyrido[2,1-a]isoquinolin-2α-ylamine (Example 8) through a Chiralpak AD column with 20% isopropanol/heptane as eluent. The retention time was 200 minutes.

MS (ISP): 354.3 (M+H)$^+$, [α]$_D$ +68.8° (c 0.520, chloroform).

Example 11 rac-9,10-Dimethoxy-3β-(6-methyl-pyridin-2-yl)-1,3,4,6,7,11bβ-hexahydro-2H-pyrido[2,1-a]isoquinolin-2α-ylamine

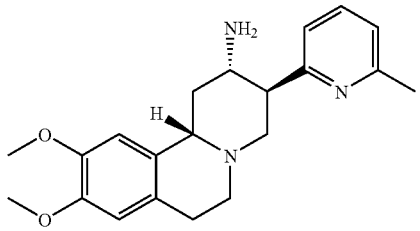

The title compound was prepared in analogy to Example 2. It was obtained as a yellow powder. This product was eluted second during chromatography (cf. Example 12).

MS (ISP): 354.4 (M+H)$^+$.

Example 12 rac-9,10-Dimethoxy-3β-(6-methyl-pyridin-2-yl)-1,3,4,6,7,11bβ-hexahydro-2H-pyrido[2,1-a]isoquinolin-2β-ylamine

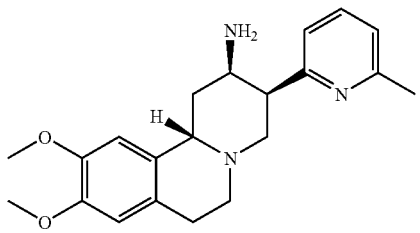

The title compound was prepared in analogy to Example 2. It was obtained as a yellow powder. This product was eluted first during chromatography (cf. Example 11).

MS (ISP): 354.4 (M+H)$^+$.

Example 13 rac-9,10-Dimethoxy-3β-(5-methyl-pyridin-2-yl)-1,3,4,6,7,11bβ-hexahydro-2H-pyrido[2,1-a]isoquinolin-2α-ylamine

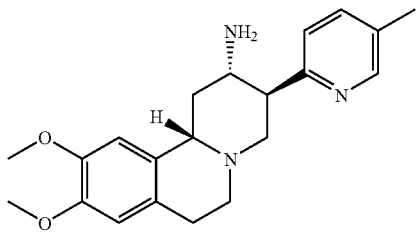

The title compound was prepared in analogy to Example 2. It was obtained as an off white powder. This product was eluted second during chromatography (cf. Example 14).

MS (ISP): 354.3 (M+H)$^+$.

Example 14 rac-9,10-Dimethoxy-3β-(5-methyl-pyridin-2-yl)-1,3,4,6,7,11bβ-hexahydro-2H-pyrido[2,1-a]isoquinolin-2β-ylamine

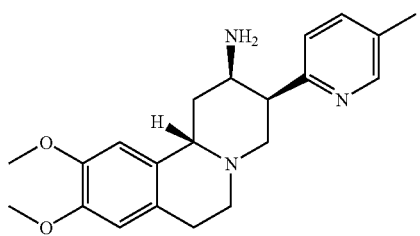

The title compound was prepared in analogy to Example 2. It was obtained as an off white powder. This product was eluted first during chromatography (cf. Example 13).
MS (ISP): 354.3 (M+H)⁺.

Example 15 rac-9,10-Dimethoxy-3β-(4-methyl-pyridin-2-yl)-1,3,4,6,7,11bβ-hexahydro-2H-pyrido[2,1-a]isoquinolin-2β-ylamine

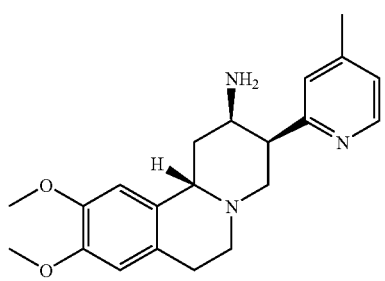

The title compound was prepared in analogy to Example 2. It was obtained as an orange powder. This product was eluted first during chromatography (cf. Example 8).
MS (ISP): 354.3 (M+H)⁺.

Example 16

9,10-Dimethoxy-3(R)-(4-methyl-pyridin-2-yl)-1,3,4,6,7,11b(R)-hexahydro-2H-pyrido[2,1-a]isoquinolin-2(S)-ylamine

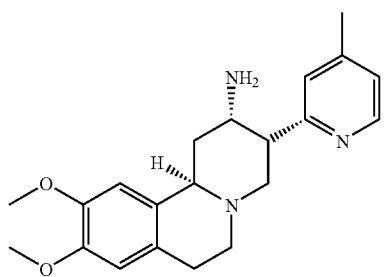

The title compound was obtained after separation of rac-9,10-Dimethoxy-3β-(4-methyl-pyridin-2-yl)-1,3,4,6,7,11bβ-hexahydro-2H-pyrido[2,1-a]isoquinolin-2β-ylamine (Example 15) through a Chiralpak AD column with 20% ethanol/heptane as eluent. The retention time was 200 minutes.

MS (ISP): 354.3 (M+H)⁺, [α]_D+129° (c 0.511, chloroform).

Example 17

9,10-Dimethoxy-3(S)-(4-methyl-pyridin-2-yl)-1,3,4,6,7,11b(S)-hexahydro-2H-pyrido[2,1-a]isoquinolin-2(R)-ylamine

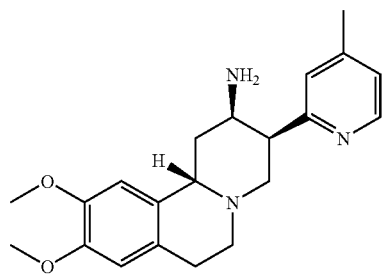

The title compound was obtained after separation of rac-9,10-Dimethoxy-3β-(4-methyl-pyridin-2-yl)-1,3,4,6,7,11bβ-hexahydro-2H-pyrido[2,1-a]isoquinolin-2β-ylamine (Example 15) through a Chiralpak AD column with 20% ethanol/heptane as eluent. The retention time was 159 minutes.

MS (ISP): 354.3 (M+H)⁺, [α]_D−127° (c 0.597, chloroform).

Example 18 rac-9,10-Dimethoxy-3β-(3-methyl-pyridin-2-yl)-1,3,4,6,7,11bβ-hexahydro-2H-pyrido[2,1-a]isoquinolin-2α-ylamine

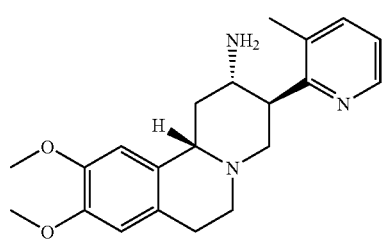

The title compound was prepared in analogy to Example 2. It was obtained as an off white powder. This product was eluted second during chromatography (cf. Example 19).
MS (ISP): 354.3 (M+H)⁺.

Example 19 rac-9,10-Dimethoxy-3β-(3-methyl-pyridin-2-yl)-1,3,4,6,7,11bβ-hexahydro-2H-pyrido[2,1-a]isoquinolin-2β-ylamine

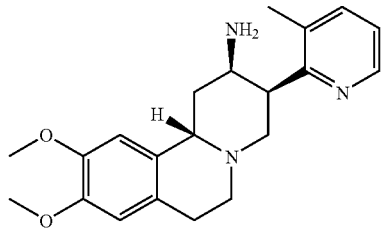

The title compound was prepared in analogy to Example 2. It was obtained as an off white powder. This product was eluted first during chromatography (cf. Example 18).
MS (ISP): 354.3 (M+H)+.

Example 20 rac-3β-(4-Ethyl-pyridin-2-yl)-9,10-dimethoxy-1,3,4,6,7,11bβ-hexahydro-2H-pyrido[2,1-a]isoquinolin-2α-ylamine

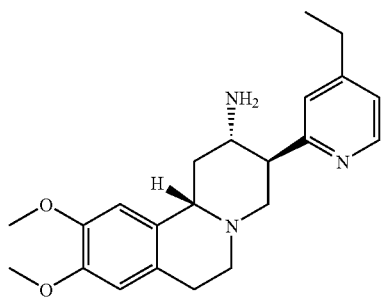

The title compound was prepared in analogy to Example 2. It was obtained as an off white powder. This product was eluted second during chromatography (cf. Example 21).
MS (ISP): 368.1 (M+H)+.

Example 21 rac-3β-(4-Ethyl-pyridin-2-yl)-9,10-dimethoxy-1,3,4,6,7,11bβ-hexahydro-2H-pyrido[2,1-a]isoquinolin-2β-ylamine

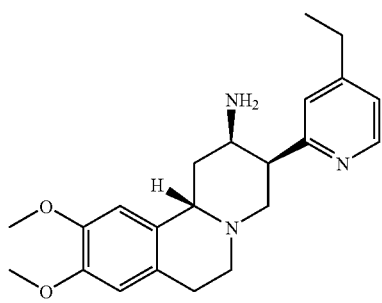

The title compound was prepared in analogy to Example 2. It was obtained as an off white powder. This product was eluted first during chromatography (cf. Example 20).
MS (ISP): 368.1 (M+H)+.

Example 22 rac-3β-(4-Ethyl-phenyl)-9,10-dimethoxy-1,3,4,6,7,11bβ-hexahydro-2H-pyrido[2,1-a]isoquinolin-2α-ylamine

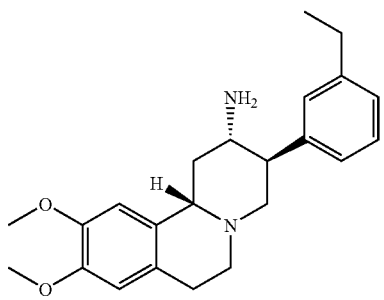

The title compound was prepared in analogy to Example 2. It was obtained as an off white powder. This product was eluted second during chromatography (cf. Example 23).
MS (ISP): 367.4 (M+H)+.

Example 23 rac-3β-(4-Ethyl-phenyl)-9,10-dimethoxy-1,3,4,6,7,11bβ-hexahydro-2H-pyrido[2,1-a]isoquinolin-2β-ylamine

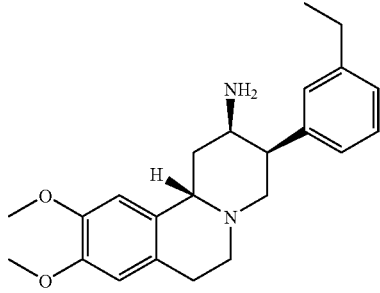

The title compound was prepared in analogy to Example 2. It was obtained as an off white powder. This product was eluted first during chromatography (cf. Example 22).
MS (ISP): 367.4 (M+H)+.

Example 24 rac-3β-(2,5-Dimethyl-phenyl)-9,10-dimethoxy-1,3,4,
6,7,11bβ-hexahydro-2H-pyrido[2,1-a]isoquinolin-
2α-ylamine

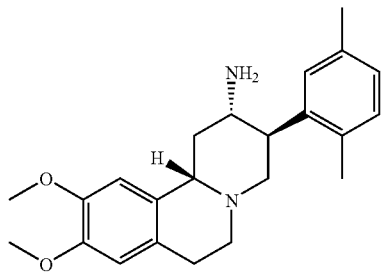

The title compound was prepared in analogy to Example 2. It was obtained as an off white powder. This product was eluted second during chromatography (cf. Example 27).
MS (ISP): 367.4 (M+H)+.

Example 25 rac-3β-(3-Cyclopropyl-phenyl)-9,10-dimethoxy-1,3,
4,6,7,11bβ-hexahydro-2H-pyrido[2,1-a]isoquinolin-
2α-ylamine

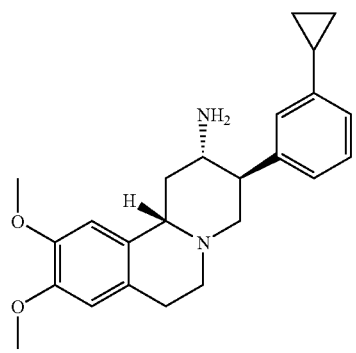

The title compound was prepared in analogy to Example 2. It was obtained as an off white powder. This product was eluted second during chromatography (cf. Example 29).
MS (ISP): 379.3 (M+H)+.

Example 26 rac-3β-(6-Methoxy-pyridin-2-yl)-9,10-dimethoxy-1,
3,4,6,7,11bβ-hexahydro-2H-pyrido[2,1-a]isoquino-
lin-2α-ylamine

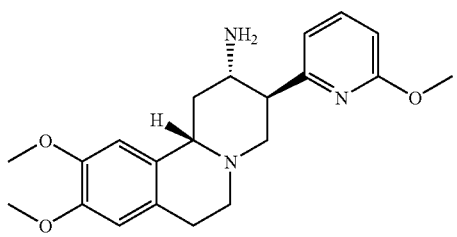

The title compound was prepared in analogy to Example 2. It was obtained as an off white powder.
MS (ISP): 370.4 (M+H)+.

Example 27 rac-3β-(2,5-Dimethyl-phenyl)-9,10-dimethoxy-1,3,4,
6,7,11bβ-hexahydro-2H-pyrido[2,1-a]isoquinolin-
2β-ylamine

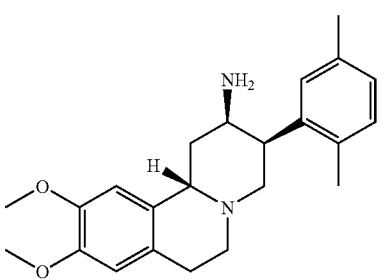

The title compound was prepared in analogy to Example 2. It was obtained as an off white powder. This product was eluted first during chromatography (cf. Example 24).
MS (ISP): 367.3 (M+H)+.

Example 28 rac-3β-(3-Isopropyl-phenyl)-9,10-dimethoxy-1,3,4,6,
7,11bβ-hexahydro-2H-pyrido[2,1-a]isoquinolin-2α-
ylamine

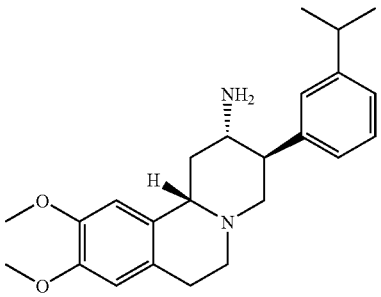

The title compound was prepared in analogy to Example 2. It was obtained as an off white powder.
MS (ISP): 381.4 (M+H)+.

Example 29 rac-3β-(3-Cyclopropyl-phenyl)-9,10-dimethoxy-1,3,
4,6,7,11bβ-hexahydro-2H-pyrido[2,1-a]isoquinolin-
2β-ylamine

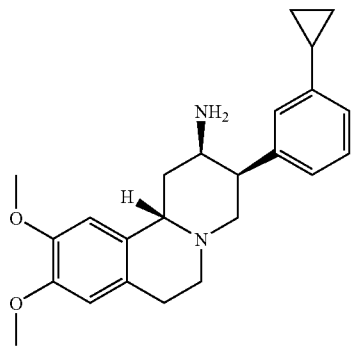

The title compound was prepared in analogy to Example 2. It was obtained as an off white powder. This product was eluted first during chromatography (cf. Example 25).

MS (ISP): 379.4 (M+H)+.

Example 30 rac-3β-(3-Fluormethyl-phenyl)-9,10-dimethoxy-1,3,4,6,7,11bβ-hexahydro-2H-pyrido[2,1-a]isoquinolin-2β-ylamine

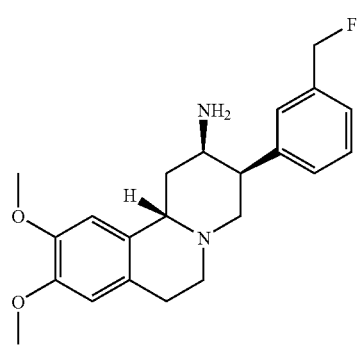

The title compound was prepared in analogy to Example 2. It was obtained as an off white powder. This product was eluted first during chromatography (cf. Example 31).

MS (ISP): 371.4 (M+H)+.

Example 31 rac-3β-(3-Fluormethyl-phenyl)-9,10-dimethoxy-1,3,4,6,7,11bβ-hexahydro-2H-pyrido[2,1-a]isoquinolin-2α-ylamine

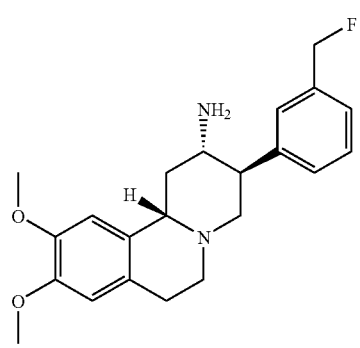

The title compound was prepared in analogy to Example 2. It was obtained as an off white powder. This product was eluted second during chromatography (cf. Example 30).

MS (ISP): 371.3 (M+H)+.

Example 32 rac-3β-(4-Methoxy-2-methyl-phenyl)-9,10-dimethoxy-1,3,4,6,7,11bβ-hexahydro-2H-pyrido[2,1-a]isoquinolin-2α-ylamine

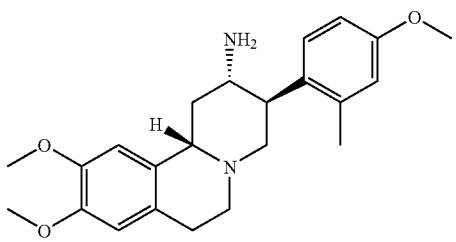

The title compound was prepared in analogy to Example 2. It was obtained as an off white powder.

MS (ISP): 383.4 (M+H)+.

Example 33 rac-9,10-Dimethoxy-3β-(3-methyl-pyrrol-1-yl)-1,3,4,6,7,11bβ-hexahydro-2H-pyrido[2,1-a]isoquinolin-2α-ylamine

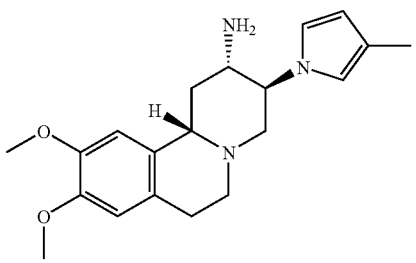

a) 2-Amino-9,10-dimethoxy-1,6,7,11b-tetrahydro-4H-pyrido[2,1-a]isoquinoline-3-carboxylic acid ethyl ester A mixture of 9,10-dimethoxy-2-oxo-1,3,4,6,7,11b-hexahydro-2H-pyrido[2,1-a]isoquinoline-3-carboxylic acid ethyl ester (*Helv. Chim. Acta* 1958, 41, 119; 4.00 g, 12.0 mmol) and ammonium acetate (13.9 g, 180 mmol) in methanol was stirred 5 h at room temperature. After evaporation of the solvent the residue was partitioned between dichloromethane and 1 M aq. sodium hydroxide solution. The organic layer was dried (MgSO4), and triturated with heptane to afford the title compound (3.71 g, 93%). Off-white solid, MS (ISP) 333.2 (M+H)+.

b) rac-2α-tert-Butoxycarbonylamino-9,10-dimethoxy-1,3,4,6,7,11bβ-hexahydro-2H-pyrido[2,1-a]isoquinoline-3β-carboxylic acid ethyl ester Trifluoroacetic acid (120 mL) was added at 0° C. to a solution of 2-amino-9,10-dimethoxy-1,6,7,11b-tetrahydro-4H-pyrido[2,1-a]isoquinoline-3-carboxylic acid ethyl ester (6.90 g, 20.8 mmol) in tetrahydrofuran (60 mL), then after 30 min the homogeneous solution was treated with sodium borohydride (1.64 g, 41.5 mmol) and stirred for another 40 min. The reaction mixture was concentrated in vacuo and the residue partitioned between 2 M aq. sodium hydroxide solution and dichloromethane. The organic layer was washed with brine, dried (MgSO$_4$) and evaporated. The residue was dissolved in dichloromethane (80 mL), and a solution of di-tert-butyl-dicarbonate (4.98 g, 22.8 mmol) in dichloromethane (50 mL) was added at room temperature. The solution was stirred overnight at room temperature, concentrated, and the residue was triturated in heptane to afford the title compound (7.44 g, 83%). Light yellow solid, MS (ISP) 435.4 (M+H)$^+$.

c) rac-2α-tert-Butoxycarbonylamino-9,10-dimethoxy-1,3,4,6,7,11bβ-hexahydro-2H-pyrido[2,1-a]isoquinoline-3β-carboxylic acid Potassium hydroxide (86%, 4.47 g, 68.5 mmol) was added to a suspension of rac-2α-tert-butoxycarbonylamino-9,10-dimethoxy-1,3,4,6,7,11bβ-hexahydro-2H-pyrido[2,1-a]isoquinoline-3β-carboxylic acid ethyl ester (7.44 g, 17.1 mmol) in tetrahydrofuran (70 mL) and water (70 mL). After heating 5 h at reflux, the mixture was concentrated in vacuo. The residue was taken up in 1M aq. potassium phosphate buffer (pH 6.85) and dichloromethane, and ethanol was added until a clear two-phase mixture was obtained. The organic layer was separated, washed with brine and evaporated to afford the title compound (6.91 g, 99%). Light yellow solid, MS (ISN) 405.3 (M−H)$^−$.

d) rac-(2α-tert-Butoxycarbonylamino-9,10-dimethoxy-1,3,4,6,7,11bβ-hexahydro-2H-pyrido[2,1-a]isoquinolin-3β-yl)-carbamic acid 2-trimethylsilanyl-ethyl ester A mixture of rac-2α-tert-butoxycarbonylamino-9,10-dimethoxy-1,3,4,6,7,11bβ-hexahydro-2H-pyrido[2,1-a]isoquinoline-3β-carboxylic acid (6.91 g, 17.0 mmol), diphenylphosphoryl azide (7.40 g, 25.6 mmol), triethylamine (1.72 g, 17.0 mmol), 2-(trimethylsilyl)-ethanol (30.2 g, 256 mmol) and toluene (40 mL) was heated 48 h at 80° C. under a gentle nitrogen stream. The reaction mixture was then concentrated in vacuo and the residue chromatographed (SiO$_2$, CH$_2$Cl$_2$/MeOH/NH$_4$OH 80:1:0.2), and the product fractions triturated in hexane/ethyl acetate 1:1 to afford the title compound (5.22 g, 59%). White solid, MS (ISP) 522.4 (M+H)$^+$.

e) rac-(3β-Amino-9,10-dimethoxy-1,3,4,6,7,11bβ-hexahydro-2H-pyrido[2,1-a]isoquinolin-2α-yl)-carbamic acid tert-butyl ester A suspension of rac-(2α-tert-butoxycarbonylamino-9,10-dimethoxy-1,3,4,6,7,11bβ-hexahydro-2H-pyrido[2,1-a]isoquinolin-3β-yl)-carbamic acid 2-trimethylsilanyl-ethyl ester (5.22 g, 10.0 mmol) in tetrabutylammonium fluoride solution (1 M in THF, 42 mL, 42 mmol) was heated 90 min at 50° C. The resultant solution was concentrated in vacuo and chromatographed (CH$_2$Cl$_2$/MeOH/NH$_4$OH 95:5:0.25) to afford the title compound (3.59 g, 95%). Light yellow solid, MS (ISP) 378.4 (M+H)$^+$.

f) rac-[3β-(3-Formyl-pyrrol-1-yl)-9,10-dimethoxy-1,3,4,6,7,11bβ-hexahydroα-2H-pyrido[2,1-a]isoquinolin-2α-yl]-carbamic acid tert-butyl ester 2,5-dimethoxytetrahydrofuran-3-carbaldehyde (73 mg, 0.41 mmol) was added to a solution of rac-(3β-amino-9,10-dimethoxy-1,3,4,6,7,11bβ-hexahydro-2H-pyrido[2,1-a]iso-quinolin-2α-yl)-carbamic acid tert-butyl ester (140 mg, 0.37 mmol) in acetic acid (1.7 mL, 29 mmol) and pyridine (1.05 mL, 13 mmol). The homogeneous solution was heated at 100° C. for 90 min, then evaporated, and the residue was chromatographed (SiO$_2$, heptane/ethyl acetate gradient) to afford the title compound (75 mg, 44%). White solid, MS (ISP) 456.3 (M+H)$^+$.

g) rac-9,10-Dimethoxy-3β-(3-methyl-pyrrol-1-yl)-1,3,4,6,7,11bβ-hexahydro-2H-pyrido[2,1-a]isoquinolin-2α-ylamine rac-[3β-(3-Formyl-pyrrol-1-yl)-9,10-dimethoxy-1,3,4,6,7,11bβ-hexahydro-2H-pyrido[2,1-a]isoquinolin-2α-yl]-carbamic acid tert-butyl ester (75 mg, 0.17 mmol) was dissolved in trifluoroacetic acid (1 mL) cooled to 0° C., treated with triethylsilane (55 mg, 0.46 mmol), stirred at 0° C. for 1 h, and concentrated in vacuo. Chromatography of the residue (SiO$_2$, CH$_2$Cl$_2$/MeOH/NH$_4$OH 95:5:0.25) produced the title compound (48 mg, 85%). White solid, MS (ISP) 342.2 (M+H)$^+$.

Example 34 rac-3β-(3-Chloro-phenyl)-9,10-dimethoxy-1,3,4,6,7,11bβ-hexahydro-2H-pyrido[2,1-a]isoquinolin-2β-ylamine hydrochloride

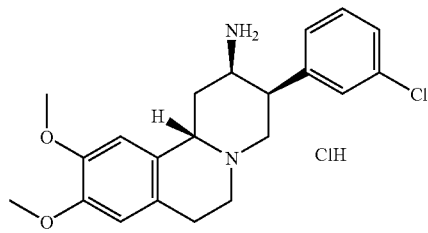

a) rac-3β-(3-chloro-phenyl)-9,10-dimethoxy-1,3,4,6,7,11bβ-hexahydro-2H-pyrido[2,1-a]isoquinolin-2-one The ketone was obtained as described in example 1a) using 1,3-dichloro-benzene as a light yellow solid (40 mg, 11%).
MS (ISP): 372.2 (M+H)$^+$.
$^1$H NMR (CDCl$_3$): δ=7.38-7.06 (m, 4H), 6.64 (s, 1H), 6.59-6.58 (m, 1H), 4-3.7 (m, 8H), 3.5-3.35 (m, 1H), 3.2-2.6 (m, 7H).

b) rac-3β-(3-Chloro-phenyl)-9,10-dimethoxy-1,3,4,6,7,11bβ-hexahydro-2H-pyrido[2,1-a]isoquinolin-2β-ylamine hydrochloride rac-3β-(3-Chloro-phenyl)-9,10-dimethoxy-1,3,4,6,7,11b-hexahydro-2H-pyrido[2,1-a]isoquinolin-2-one (60 mg, 0.16 mmol) was dissolved in methanol (10 ml) and methylene chloride (5 ml). Ammonium acetate (248 mg, 3.2 mmol) was added and the reaction was stirred at room temperature over night. Sodium cyanoborohydride (13 mg, 0.2 mmol) was added. After stirring for one hour at room temperature the reaction mixture was diluted with water and extracted 3 times with methylene chloride. The combined organic layers were washed with brine, dried over sodium sulfate, and concentrated in vacuo. The residue was chromatographed on silica gel (CH2Cl2/MeOH/25% aq NH3=97/3/0.5) to afford the product eluting first as one of the diastereomers. It was dissolved in diethyl ether and HCl in ether was added. The solvent was evaporated to leave the product as a light yellow solid (22 mg, 33%).

MS (ISP): 372.3 (M+H)⁺.

¹H NMR (CDCl₃): δ=7.4-7.10 (m, 4H), 6.69 (s, 1H), 6.62 (s, 1H), 3.9-3.7 (m, 6H), 3.6-2.35 (m, 10H), 2-1.9 (m, 1H). ISP-MS: m/z=373.3 (M+H).

Example 35 rac-3β-(3-Chloro-phenyl)-9,10-dimethoxy-1,3,4,6,7,11bβ-hexahydro-2H-pyrido[2,1-a]isoquinolin-2α-ylamine hydrochloride

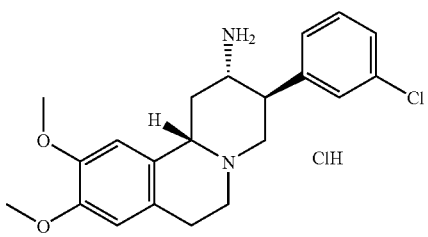

The product was obtained in the final chromatography described in Example 1b) eluting as second compound. The product was dissolved in diethyl ether and 1N HCl in diethyl ether was added. The solvent was evaporated to leave the product as a light yellow solid (26 mg).

MS (ISP): 373.3 (M+H)⁺.

¹H NMR (CDCl₃): δ=7.31-7.15 (m, 4H), 6.73 (s, 1H), 6.60 (s, 1H), 3.9-3.8 (m, 7H), 3.4-2.2 (m, 9H).

Example 36 rac-[2-(2α-Amino-9,10-dimethoxy-1,3,4,6,7,11bβ-hexahydro-2H-pyrido[2,1-a]isoquinolin-3β-yl)-pyridin-4-yl]-methanol

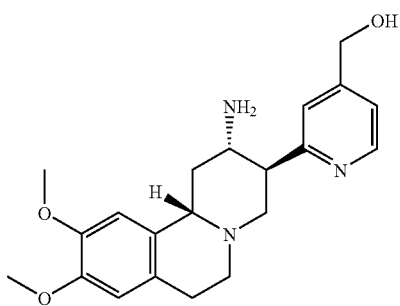

a) 2-Bromo-4-(tert-butyl-dimethyl-silanyloxymethyl)-pyridine

To a solution of 2-bromo-4-(hydroxymethyl)pyridine (Lancaster, [CAS 118289-16-0]) (7.3 g) and imidazole (2.65 g) in dichloromethane (80 ml) was added dropwise over 15 minutes at 0-5° C. a solution of tert-butyldimethylsilyl chloride (5.85 g) in dichloro-methane (20 ml). The reaction mixture was stirred at 0-5° C. for 3 h, poured onto ice/water and extracted with dichloromethane. The organic phase was washed with water, sat. sodiumhydrogencarbonate solution and brine, dried over magnesium sulphate and concentrated. The crude compound was filtered over silica gel (200 g) with dichloro-methane as eluent. The product containing fractions were evaporated to dryness to obtain 2-bromo-4-(tert-butyl-dimethyl-silanyloxymethyl)-pyridine (10.3 g) as a colourless liquid.

MS (ISP): 302.0, 304.1 (M+H)⁺.

b) rac-3β-[4-(tert-Butyl-dimethyl-silanyloxymethyl)-pyridin-2-yl]-9,10-dimethoxy-1,3,4,6,7,11bβ-hexahydro-pyrido[2,1-a]isoquinolin-2-one A mixture of palladium acetate (0.84 g), sodium tert-butoxide (9.8 g) and rac-9,10-dimethoxy-1,3,4,6,7,11bβ-hexahydro-2H-benzo[a]quinolizin-2-one (8.90 g) [D. Beke, C. Szantay, Chem. Ber. 95, 2132 (1962)] was evaporated under high vacuum at 80° C. and flushed with argon three to five times. Degassed tetrahydrofuran (200 ml) was added at room temperature under argon. The reaction mixture was stirred for 15 minutes at room temperature, and tri-tert-butylphosphine (0.76 g) and 2-bromo-4-(tert.-butyl-dimethyl-silanyloxymethyl)-pyridine (10.3 g) were added simultaneously with a syringe. The reaction mixture was stirred at 20-25° C. under argon for 18 hours. The crude reaction mixture was poured on ice/water (1l), neutralized with 2N hydrochloric acid and extracted with tert.-butylmethyl ether. The organic phase was washed with water and brine, dried over magnesium sulfate and concentrated. The residue was purified by column chromatography (silica gel, 400 g) using cyclohexane/ethyl acetate 1:1 as eluent to yield rac-3β-[4-(tert-butyl-dimethyl-silanyloxymethyl)-pyridin-2-yl]-9,10-dimethoxy-1,3,4,6,7,11bβ-hexahydro-pyrido[2,1-a]isoquinolin-2-one (6.9 g) as a yellow foam.

MS (ISP): 483.4 (M+H)⁺.

c) rac-3β-(4-Hydroxymethyl-pyridin-2-yl)-9,10-dimethoxy-1,3,4,6,7,11bβ-hexahydro-pyrido[2,1-a]isoquinolin-2-one To a solution of rac-3β-[4-(tert.-butyl-dimethyl-silanyloxymethyl)-pyridin-2-yl]-9,10-dimethoxy-1,3,4,6,7,11bβ-hexahydro-pyrido[2,1-a]isoquinolin-2-one (6.85 g) in tetrahydrofuran (340 ml) was added tetrabutylammonium fluoride trihydrate (11.2 g). The reaction mixture was stirred at room temperature for 2 h and concentrated. To the residue was added water/ice, and it was extracted with dichloromethane. The organic phase was washed with water and brine, dried over magnesium sulphate and concentrated. The residue was purified by chromatography on silica gel using dichloromethane/methanol/ammonium hydroxide as eluent to obtain rac-3β-(4-hydroxymethyl-pyridin-2-yl)-9,10-dimethoxy-1,3,4,6,7,11bβ-hexahydro-pyrido[2,1-a]isoquinolin-2-one (4.6 g) as a yellow amorphous powder.

MS (ISP): 369.1 (M+H)⁺ d) rac-3β-(4-Hydroxymethyl-pyridin-2-yl)-9,10-dimethoxy-1,3,4,6,7,11bβ-hexahydro-pyrido[2,1-a]isoquinolin-2-one oxime This compound was prepared in analogy to example 2b starting from rac-3β-(4-hydroxymethyl-pyridin-2-yl)-9,10-dimethoxy-1,3,4,6,7,11bβ-hexahydro-pyrido[2,1-a]isoquinolin-2-one (4.6 g), hydroxylamine hydrochloride (0.954 g) and sodium acetate (1.12 g) in ethanol (140 ml) to obtain rac-3β-(4-hydroxymethyl-pyridin-2-yl)-9,10-dimethoxy-1, 3,4,6,7,11bβ-hexahydro-pyrido[2,1-a]isoquinolin-2-one oxime (4.67 g) as light yellow crystals.
MS (ISP): 384.3 (M+H)+ e) rac-[2-(2α-Amino-9,10-dimethoxy-1,3,4,6,7,11bβ-hexahydro-2H-pyrido[2,1-a]isoquinolin-3β-yl)-pyridin-4-yl]-methanol This compound was prepared in analogy to example 2c starting from rac-3β-(4-hydroxymethyl-pyridin-2-yl)-9,10-dimethoxy-1,3,4,6,7,11bβ-hexahydro-pyrido[2,1-a]isoquinolin-2-one oxime (4.60 g), to obtain after chromatography on silica gel with dichloromethane/methanol/ammonium hydroxide rac-[2-(2α-amino-9,10-dimethoxy-1,3,4,6,7,11b-hexahydro-2H-pyrido[2,1-a]isoquinolin-3β-yl)-pyridin-4-yl]-methanol (2.16 g) as a light yellow solid.
MS (ISP): 370.3 (M+H)+

Example 37 rac-3β-(4-Fluormethyl-pyridin-2-yl)-9,10-dimethoxy-1,3,4,6,7,11bβ-hexahydro-2H-pyrido[2,1-a]isoquinolin-2α-ylamine hydrochloride

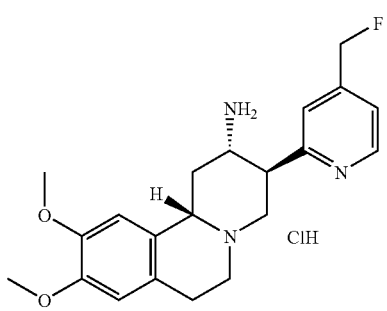

a) [rac-3β-(4-Hydroxymethyl-pyridin-2-yl)-9,10-dimethoxy-1,3,4,6,7,11bβ-hexahydro-2H-pyrido[2,1-a]isoquinolin-2α-yl]-carbamic acid tert-butyl ester To a solution of rac-[2-(2α-amino-9,10-dimethoxy-1,3,4,6,7,11bβ-hexahydro-2H-pyrido[2,1-a]isoquinolin-3β-yl)-pyridin-4-yl]-methanol (2.15 g) in dichloromethane (215 ml) was added di-tert.-butyl dicarbonate (1.27 g). The reaction mixture was refluxed for 2 h, concentrated, and the residue was purified by chromatography on silica gel using dichloromethane/methanol/ammonium hydroxide as eluent to obtain [rac-3β-(4-hydroxymethyl-pyridin-2-yl)-9,10-dimethoxy-1,3,4,6,7,11b β-hexahydro-2H-pyrido[2,1-a]isoquinolin-2α-yl]-carbamic acid tert-butyl ester (2.35 g) as light yellow solid.
MS (ISP): 470.3 (M+H)+ b) [rac-3β-(4-Fluoromethyl-pyridin-2-yl)-9,10-dimethoxy-1,3,4,6,7,11bβ-hexahydro-2H-pyrido[2,1-a]isoquinolin-2α-yl]-carbamic acid tert-butyl ester To a solution of [rac-3β-(4-hydroxymethyl-pyridin-2-yl)-9,10-dimethoxy-1,3,4,6,7,11bβ-hexahydro-2H-pyrido[2,1-a]isoquinolin-2α-yl]-carbamic acid tert-butyl ester (0.5 g) in dichloromethane (15 ml) was added at 0° C. diethylaminosulfur-trifluoride (0.515 g). The reaction mixture was stirred at 0-5° C. for 2 h, quenched with ice/bicarbonate, extracted with dichloromethane. The organic phase was washed with brine, dried over magnesium sulphate and concentrated. The residue was purified by chromatography on silica gel (50 g) with dichloromethane/methanol 2, 4 and 8% as eluent to obtain [rac-3β-(4-fluoromethyl-pyridin-2-yl)-9,10-dimethoxy-1,3,4,6,7,11bβ-hexahydro-2H-pyrido[2,1-a]isoquinolin-2α-yl]-carbamic acid tert-butyl ester (0.15 g) as a yellow foam.
MS (ISP): 472.4 (M+H)+ c) rac-3β-(4-Fluormethyl-pyridin-2-yl)-9,10-dimethoxy-1,3,4,6,7,11bβ-hexahydro-2H-pyrido[2,1-a]isoquinolin-2α-ylamine hydrochloride To a solution of [rac-3β-(4-fluoromethyl-pyridin-2-yl)-9,10-dimethoxy-1,3,4,6,7,11bβ-hexahydro-2H-pyrido[2,1-a] isoquinolin-2α-yl]-carbamic acid tert-butyl ester (0.095 g) in dioxane (5.0 ml) was added 4 molar HCl/dioxane (5.0 ml). The reaction mixture was stirred over night at room temperature, and diethyl ether (75 ml) was added to precipitate the hydrochloride. The crystals were filtered, washed with ether and dried to obtain the title compound (0.065 g) as a light yellow solid.
MS (ISP): 372.1 (M+H)+

Example 38 rac-3β-(4-Fluormethyl-pyridin-2-yl)-9,10-dimethoxy-1,3,4,6,7,11bβ-hexahydro-2H-pyrido[2,1-a]isoquinolin-2α-ylamine

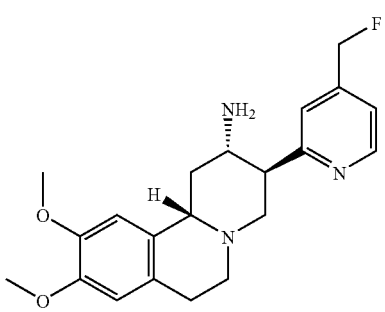

A solution of rac-3β-(4-fluormethyl-pyridin-2-yl)-9,10-dimethoxy-1,3,4,6,7,11bβ-hexahydro-2H-pyrido[2,1-a]isoquinolin-2α-ylamine hydrochloride (0.040 g) in methanol/water 1:1 (5 ml) was filtrated over basic ion exchange resin (IRA-400) using the same solvent as eluent. The product fractions were combined and evaporated to dryness to obtain the title compound (0.025 g) as orange foam.
MS (ISP): 372.1 (M+H)+

GALENICAL EXAMPLES

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |

-continued

| Ingredients | Per tablet | |
|---|---|---|
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Ingredients | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Ingredients | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Ingredients | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

What is claimed is:
1. A compound of formula (I)

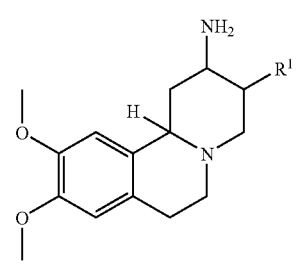

wherein
R¹ is selected from the group consisting of

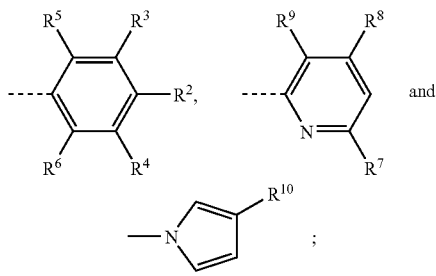

R², R⁴ and R⁵ are hydrogen;
R³ and R⁶ are each independently lower alkyl, halogenated lower alkyl, halogen or cycloalkyl;
R⁷, R⁸ and R⁹ are each independently selected from the group consisting of hydrogen, lower alkyl, lower alkoxy, lower hydroxyalkyl and halogenated lower alkyl; provided that R⁷, R⁸ and R⁹ not all hydrogen; and
R¹⁰ is lower alkyl or halogenated lower alkyl; and
or a pharmaceutically acceptable salt thereof.

2. The compound according to claim 1, wherein R¹ is

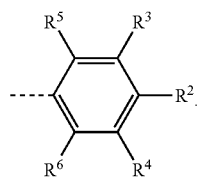

3. The compound according to claim 1 wherein R², R⁴ and R⁵ are hydrogen and R³ and R⁶ are each independently lower alkyl or halogen.

4. The compound according to claim 1, wherein R¹ is

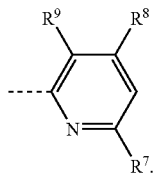

5. The compound according to claim 1 wherein R⁷ and R⁹ are each hydrogen and R⁸ is lower alkyl or lower alkoxy.

6. The compound according to claim 1, wherein R¹ is

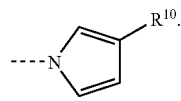

7. The compound according to claim 1, selected from the group consisting of:
rac-9,10-dimethoxy-3β-m-tolyl-1,3,4,6,7,11bβ-hexahydro-2H-pyrido[2,1-a]isoquinolin-2-ylamine hydrochloride;
rac-9,10-dimethoxy-3β-m-tolyl-1,3,4,6,7,11bβ-hexahydro-2H-pyrido[2,1-a] isoquinolin-2β-ylamine;
9,10-dimethoxy-3(R)-m-tolyl-1,3,4,6,7,11b(R)-hexahydro-2H-pyrido[2,1-a]isoquinolin-2(S)-ylamine;
9,10-dimethoxy-3(S)-m-tolyl-1,3,4,6,7,11b(S)-hexahydro-2H-pyrido[2,1-a]isoquinolin-2(R)-ylamine;
rac-9,10-dimethoxy-3β-m-tolyl-1,3,4,6,7,11bβ-hexahydro-2H-pyrido[2,1-a]isoquinolin-2α-ylamine;
9,10-dimethoxy-3(S)-m-tolyl-1,3,4,6,7,11b(S)-hexahydro-2H-pyrido[2,1-a]isoquinolin-2(S)-ylamine;
9,10-dimethoxy-3(R)-m-tolyl-1,3,4,6,7,11b(R)-hexahydro-2H-pyrido[2,1-a]isoquinolin-2(R)-ylamine;
rac-9,10-dimethoxy-3β-(4-methyl-pyridin-2-yl)-1,3,4,6,7,11bβ-hexahydro-2H-pyrido[2,1-a]isoquinolin-2α-ylamine;
9,10-dimethoxy-3(S)-(4-methyl-pyridin-2-yl)-1,3,4,6,7,11b(S)-hexahydro-2H-pyrido[2,1-a]isoquinolin-2(S)-ylamine; and
9,10-dimethoxy-3(R)-(4-methyl-pyridin-2-yl)-1,3,4,6,7,11b(R)-hexahydro-2H-pyrido[2,1-a]isoquinolin-2(R)-ylamine;
or a pharmaceutically acceptable salt thereof.

8. The compound according to claim 1, selected from the group consisting of:
rac-9,10-dimethoxy-3β-(6-methyl-pyridin-2-yl)-1,3,4,6,7,11bβ-hexahydro-2H-pyrido[2,1-a]isoquinolin-2α-ylamine;
rac-9,10-dimethoxy-3β-(6-methyl-pyridin-2-yl)-1,3,4,6,7,11bβ-hexahydro-2H-pyrido[2,1-a]isoquinolin-2α-ylamine;
rac-9,10-dimethoxy-3β-(5-methyl-pyridin-2-yl)-1,3,4,6,7,11bβ-hexahydro-2H-pyrido[2,1-a]isoquinolin-2α-ylamine;
rac-9,10-dimethoxy-3β-(5-methyl-pyridin-2-yl)-1,3,4,6,7,11bβ-hexahydro-2H-pyrido[2,1-a]isoquinolin-2β-ylamine;
rac-9,10-dimethoxy-3β-(4-methyl-pyridin-2-yl)-1,3,4,6,7,11bβ-hexahydro-2H-pyrido[2,1-a]isoquinolin-2β-ylamine;
9,10-dimethoxy-3(R)-(4-methyl-pyridin-2-yl)-1,3,4,6,7,11b(R)-hexahydro-2H-pyrido[2,1-a]isoquinolin-2(S)-ylamine;
9,10-dimethoxy-3(S)-(4-methyl-pyridin-2-yl)-1,3,4,6,7,11b(S)-hexahydro-2H-pyrido[2,1-a]isoquinolin-2(R)-ylamine;
rac-9,10-dimethoxy-3β-(3-methyl-pyridin-2-yl)-1,3,4,6,7,11bβ-hexahydro-2H-pyrido[2,1-a]isoquinolin-2α-ylamine;
rac-9,10-dimethoxy-3β-(3-methyl-pyridin-2-yl)-1,3,4,6,7,11bβ-hexahydro-2H-pyrido[2,1-a]isoquinolin-2β-ylamine; and
rac-3β-(4-ethyl-pyridin-2-yl)-9,10-dimethoxy-1,3,4,6,7,11bβ-hexahydro-2H-pyrido[2,1-a] isoquinolin-2α-ylamine;
or a pharmaceutically acceptable salt thereof.

9. The compound according to claim 1, selected from the group consisting of:
rac-3β-(4-ethyl-pyridin-2-yl)-9,10-dimethoxy-1,3,4,6,7,11bβ-hexahydro-2H-pyrido[2,1-a]isoquinolin-2β-ylamine;
rac-3β-(4-ethyl-phenyl)-9,10-dimethoxy-1,3,4,6,7,11bβ-hexahydro-2H-pyrido[2,1-a]isoquinolin-2α-ylamine;
rac-3β-(4-ethyl-phenyl)-9,10-dimethoxy-1,3,4,6,7,11bβ-hexahydro-2H-pyrido[2,1-a]isoquinolin-2β-ylamine;
rac-3β-(2,5-dimethyl-phenyl)-9,10-dimethoxy-1,3,4,6,7,11bβ-hexahydro-2H-pyrido[2,1-a]isoquinolin-2α-ylamine;

rac-3β-(3-cyclopropyl-phenyl)-9,10-dimethoxy-1,3,4,6,7,11bβ-hexahydro-2H-pyrido[2,1-a]isoquinolin-2α-ylamine;

rac-3β-(6-methoxy-pyridin-2-yl)-9,10-dimethoxy-1,3,4,6,7,11bβ-hexahydro-2H-pyrido[2,1-a]isoquinolin-2α-ylamine;

rac-3β-(2,5-dimethyl-phenyl)-9,10-dimethoxy-1,3,4,6,7,11bβ-hexahydro-2H-pyrido[2,1-a]isoquinolin-2β-ylamine;

rac-3β-(3-isopropyl-phenyl)-9,10-dimethoxy-1,3,4,6,7,11bβ-hexahydro-2H-pyrido[2,1-a]isoquinolin-2α-ylamine;

rac-3β-(3-cyclopropyl-phenyl)-9,10-dimethoxy-1,3,4,6,7,11bβ-hexahydro-2H-pyrido[2,1-a]isoquinolin-2β-ylamine; and rac-3β-(3-fluormethyl-phenyl)-9,10-dimethoxy-1,3,4,6,7,11bβ-hexahydro-2H-pyrido[2,1-a]isoquinolin-2β-ylamine;

or a pharmaceutically acceptable salt thereof.

10. The compound according to claim 1, selected from the group consisting of: rac-3β-(3-fluormethyl-phenyl)-9,10-dimethoxy-1,3,4,6,7,11bβ-hexahydro-2H-pyrido[2,1-a]isoquinolin-2α-ylamine;

rac-3β-(4-methoxy-2-methyl-phenyl)-9,10-dimethoxy-1,3,4,6,7,11bβ-hexahydro-2H-pyrido[2,1-a]isoquinolin-2α-ylamine;

rac-9,10-dimethoxy-3β-(3-methyl-pyrrol-1-yl)-1,3,4,6,7,11bβ-hexahydro-2H-pyrido[2,1-a]isoquinolin-2α-ylamine;

rac-3β-(3-chloro-phenyl)-9,10-dimethoxy-1,3,4,6,7,11bβ-hexahydro-2H-pyrido[2,1-a]isoquinolin-2β-ylamine hydrochloride;

rac-3β-(3-chloro-phenyl)-9,10-dimethoxy-1,3,4,6,7,11bβ-hexahydro-2H-pyrido[2,1-a]isoquinolin-2α-ylamine hydrochloride;

rac-[2-(2α-amino-9,10-dimethoxy-1,3,4,6,7,11bβ-hexahydro-2H-pyrido[2,1-a]isoquinolin-3β-yl)-pyridin-4-yl]-methanol;

rac-3β-(4-fluoromethyl-pyridin-2-yl)-9,10-dimethoxy-1,3,4,6,7,11bβ-hexahydro-2H-pyrido[2,1-a]isoquinolin-2α-ylamine hydrochloride; and rac-3β-(4-fluoromethyl-pyridin-2-yl)-9,10-dimethoxy-1,3,4,6,7,11bβ-hexahydro-2H-pyrido[2,1-a]isoquinolin-2α-ylamine;

or a pharmaceutically acceptable salt thereof.

11. The compound according to claim 1, selected from the group consisting of:

9,10-dimethoxy-3(R)-m-tolyl-1,3,4,6,7,11b(R)-hexahydro-2H-pyrido[2,1-a]isoquinolin-2(S)-ylamine;

9,10-dimethoxy-3(S)-m-tolyl-1,3,4,6,7,11b(S)-hexahydro-2H-pyrido[2,1-a]isoquinolin-2(S)-ylamine;

9,10-dimethoxy-3(S)-(4-methyl-pyridin-2-yl)-1,3,4,6,7,11b(S)-hexahydro-2H-pyrido[2,1-a]isoquinolin-2(S)-ylamine;

9,10-dimethoxy-3(R)-(4-methyl-pyridin-2-yl)-1,3,4,6,7,11b(R)-hexahydro-2H-pyrido[2,1-a]isoquinolin-2(S)-ylamine;

rac-3β-(4-ethyl-pyridin-2-yl)-9,10-dimethoxy-1,3,4,6,7,11bβ-hexahydro-2H-pyrido[2,1-a]isoquinolin-2α-ylamine; and rac-3β-(4-ethyl-pyridin-2-yl)-9,10-dimethoxy-1,3,4,6,7,11bβ-hexahydro-2H-pyrido[2,1-a]isoquinolin-2β-ylamine;

or a pharmaceutically acceptable salt thereof.

12. The compound according to claim 1, selected from the group consisting of:

rac-3β-(2,5-dimethyl-phenyl)-9,10-dimethoxy-1,3,4,6,7,11bβ-hexahydro-2H-pyrido[2,1-a]isoquinolin-2α-ylamine;

rac-3β-(2,5-dimethyl-phenyl)-9,10-dimethoxy-1,3,4,6,7,11bβ-hexahydro-2H-pyrido[2,1-a]isoquinolin-2β-ylamine;

rac-3β-(3-chloro-phenyl)-9,10-dimethoxy-1,3,4,6,7,11bβ-hexahydro-2H-pyrido[2,1-a]isoquinolin-2β-ylamine hydrochloride;

rac-3β-(3-chloro-phenyl)-9,10-dimethoxy-1,3,4,6,7,11bβ-hexahydro-2H-pyrido[2,1-a]isoquinolin-2□-ylamine hydrochloride;

rac-3β-(3-fluormethyl-phenyl)-9,10-dimethoxy-1,3,4,6,7,11bβ-hexahydro-2H-pyrido[2,1-a]isoquinolin-2β-ylamine;

rac-3β-(3-fluormethyl-phenyl)-9,10-dimethoxy-1,3,4,6,7,11bβ-hexahydro-2H-pyrido[2,1-a]isoquinolin-2α-ylamine; and rac-9,10-dimethoxy-3β-(3-methyl-pyrrol-1-yl)-1,3,4,6,7,11bβ-hexahydro-2H-pyrido[2,1-a]isoquinolin-2α-ylamine or a pharmaceutically acceptable salt thereof.

13. A pharmaceutical composition, comprising a therapeutically effective amount of a compound according to claim 1 or a pharmaceutically acceptable salt thereof and a pharmaceutically acceptable carrier.

* * * * *